US009188874B1

(12) United States Patent
Johnson

(10) Patent No.: US 9,188,874 B1
(45) Date of Patent: Nov. 17, 2015

(54) SPOT-ARRAY IMAGING SYSTEM FOR MASKLESS LITHOGRAPHY AND PARALLEL CONFOCAL MICROSCOPY

(75) Inventor: Kenneth C. Johnson, Santa Clara, CA (US)

(73) Assignee: Kenneth C. Johnson, Santa Clara, CA (US)

( * ) Notice: Subject to any disclaimer, the term of this patent is extended or adjusted under 35 U.S.C. 154(b) by 543 days.

(21) Appl. No.: 13/523,843

(22) Filed: Jun. 14, 2012

Related U.S. Application Data

(60) Provisional application No. 61/498,427, filed on Jun. 17, 2011, provisional application No. 61/521,684, filed on Aug. 9, 2011, provisional application No. 61/525,125, filed on Aug. 18, 2011, provisional application No. 61/531,981, filed on Sep. 7, 2011, provisional application No. 61/549,158, filed on Oct. 19, 2011.

(51) Int. Cl.
  *G03F 7/20* (2006.01)
  *G01B 9/04* (2006.01)
  *G01N 21/88* (2006.01)
  *G02B 21/00* (2006.01)

(52) U.S. Cl.
  CPC .............. *G03F 7/70308* (2013.01); *G01B 9/04* (2013.01); *G01N 21/8803* (2013.01); *G01N 21/8806* (2013.01); *G02B 21/002* (2013.01); *G02B 21/0024* (2013.01); *G02B 21/0036* (2013.01); *G02B 21/0052* (2013.01); *G03F 7/70191* (2013.01); *G03F 7/70275* (2013.01)

(58) Field of Classification Search
  None
  See application file for complete search history.

(56) References Cited

U.S. PATENT DOCUMENTS

| | | | |
|---|---|---|---|
| 5,161,057 | A | 11/1992 | Johnson |
| 5,212,588 | A | 5/1993 | Viswanathan et al. |
| 5,589,982 | A | 12/1996 | Faklis et al. |
| 5,900,637 | A | 5/1999 | Smith |
| 6,133,986 | A | 10/2000 | Johnson |
| 6,177,980 | B1 | 1/2001 | Johnson |

(Continued)

OTHER PUBLICATIONS

Bass, M., *Handbook of Optics*, 2nd ed. (Optical Society of America, Washington, DC, 1995,) vol. 2, pp. 1.23-26 and 18.15, 7 pages.

(Continued)

*Primary Examiner* — Gordon J Stock, Jr.
(74) *Attorney, Agent, or Firm* — Kilpatrick Townsend & Stockton LLP

(57) ABSTRACT

In a scanned-spot-array lithography system, a modulated array of radiant-energy source spots is imaged by a projection lens onto a printing surface, which is scanned in synchronization with the spot modulation to print a synthesized, high-resolution raster image. Similarly, in a scanned-spot-array microscopy system, an array of radiant-energy source spots is imaged by a projection lens onto an inspection surface, and radiation reflected from or transmitted through the image spots is collected and detected to acquire a synthesized, high-resolution raster image of the surface. In either case, the spot-generation optics can be configured to counterbalance and neutralize imperfect imaging characteristics of the projection lens, enabling perfectly flat-field, distortion-free, and aberration-free point imaging of the entire spot array. The spot-generation optics can also be further configured to achieve narrow-band achromatization of the optical system, and to optimally control the intensity and polarization characteristics of the image-plane radiation.

35 Claims, 23 Drawing Sheets

(56) References Cited

U.S. PATENT DOCUMENTS

| | | | |
|---|---|---|---|
| 6,214,633 B1 | 4/2001 | Clark et al. | |
| 6,238,852 B1 | 5/2001 | Klosner | |
| 6,331,710 B1 | 12/2001 | Wang et al. | |
| 6,424,404 B1 | 7/2002 | Johnson | |
| 6,498,685 B1 | 12/2002 | Johnson | |
| 6,639,201 B2 | 10/2003 | Almogy et al. | |
| 6,897,941 B2 | 5/2005 | Almogy | |
| 6,960,773 B2 | 11/2005 | Menon et al. | |
| 6,967,711 B2* | 11/2005 | Gui | 355/67 |
| 7,079,306 B2 | 7/2006 | McGeoch | |
| 7,116,402 B2* | 10/2006 | Gui | 355/57 |
| 7,116,405 B2 | 10/2006 | Johnson | |
| 7,239,373 B2 | 7/2007 | Tinnemans et al. | |
| 7,251,020 B2* | 7/2007 | Gui | 355/67 |
| 7,846,649 B2 | 12/2010 | Tirosh et al. | |
| 7,859,647 B2 | 12/2010 | Bleeker et al. | |
| 8,390,787 B2* | 3/2013 | Gui et al. | 355/69 |
| 8,687,277 B2 | 4/2014 | Johnson | |
| 8,994,920 B1 | 3/2015 | Johnson | |
| 2008/0298552 A1 | 12/2008 | Derra et al. | |
| 2009/0046299 A1 | 2/2009 | Menon et al. | |
| 2010/0079739 A1 | 4/2010 | Goehnermeier et al. | |
| 2010/0097703 A1 | 4/2010 | Menon et al. | |
| 2013/0258305 A1 | 10/2013 | Johnson | |
| 2014/0285878 A1* | 9/2014 | Escuti et al. | 359/352 |

OTHER PUBLICATIONS

Bomzon et al., "Radially and azimuthally polarized beams generated by space-variant dielectric subwavelength gratings," Optics Letters vol. 27(5), 2002, pp. 285-287.
Brandt, et al., "LPP EUV Source Development for HVM," in Proceedings of SPIE vol. 6517, Emerging Lithographic Technologies XI, M. J. Lercel, Ed., 65170Q, 2007, 10 pages.
Burnett et al., "Birefringence issues with uniaxial crystals as last lens elements for high-index immersion lithography," Proceedings SPIE 7274, 2009, pp. 727421-1 . . . 11.
Constancias et al., "Fabrication of large area ultrathin silicon membrane: Application for high efficiency extreme ultraviolet diffraction gratings," Journal of Vacuum Science & Technology, 2010, B 28, pp. 194-197.
Fritze et al., "Gratings of regular arrays and trim exposures for ultralarge scale integrated circuit phase-shift lithography," Journal of Vacuum Science & Technology, 2001, B 19(6), 2366-2370.
Goldstein et al., "EUV micro-exposure tool at 0.5 NA for sub-16 nm lithography," Optics Letters, 2008, 33(4), pp. 2995-2997.
Goodman, J. W., *An Introduction to Fourier Optics*, 1996, Sect. 3.4.2, pp. 44-45, 4 pages, McGraw-Hill.
Jung et al., "Selective dry etching of attenuated phase-shift mask materials for extreme ultraviolet lithography using inductively coupled plasmas," Journal of Vacuum Science & Technology, 2009, B 27, pp. 2361-2365.
Kingslake, R., *Lens Design Fundamentals*, Academic Press, London, 1978, pp. 89-92, 6 pages.

Menon et al., "Absorbance-modulation optical lithography," Journal of the Optical Society of America A, 2006, vol. 23, Issue 9, pp. 2290-2294.
Menon et al., "Design of diffractive lenses that generate optical nulls without phase singularities," Journal of the Optical Society of America A, 2009, vol. 26, Issue 2, pp. 297-304.
Miyamoto, K., "The Phase Fresnel Lens," Journal of the Optical Society of America, vol. 51(1), 1961, pp. 17-20.
Nam et al., "Potential of Solid Immersion Lithography using I-line and KrF light source," Proceedings SPIE 5745, 2005, pp. 1049-1055.
Pelletier et al., "Aluminum nanowire polarizing grids: Fabrication and analysis," Applied Physics Letters, vol. 88, 2006, pp. 211114-1 . . . 3.
Richter et al., "Design considerations of form birefringent microstructures," Applied Optics, 1995, vol. 34(14), pp. 2421-2429.
Salmassi et al., "Multilayer phase-only diffraction gratings: Fabrication and application to extreme ultraviolet optics," Journal of Vacuum Science & Technology, B 25, 2007, 17 pages.
Smith et al., "25nm Immersion Lithography at a 193nm Wavelength," Proceedings SPIE 5745, 2004, pp. 141-147.
Tsai et al., "Fabrication of spiral-phase diffractive elements using scanning-electron beam-lithography," Journal of Vacuum Science & Technology, 2007, B 25, pp. 2068-2071.
Tsai et al., "Far-Field Optical Imaging at the Nanoscale via Absorbance Modulation," *Novel Techniques in Microscopy*, OSA Technical Digest (CD,) Optical Society of America, 2009, paper NMA2, 3 pages.
Watanabe et al., "Generation of a doughnut-shaped beam with a spiral phase plate," Review of Scientific Instruments, vol. 75, 2004, 5131-5135.
Williamson, D. M., "Evolution of ring-field systems in microlithography," SPIE Proceedings, 1998, vol. 3482, 8 pages.
Yoder, "Opto-Mechanical Systems Design, Third Edition," CRC Press, 2006, pp. 368-370, 5 pages.
Zimmerman et al., "High Index 193 nm Immersion Lithography: The Beginning or the End of the Road," Proceedings of SPIE 7274, 2009, pp. 727420-1 . . . 11.
U.S. Appl. No. 13/103,874, filed May 9, 2011 for Johnson.
U.S. Appl. No. 61/498,427, filed Jun. 17, 2011 for Johnson.
U.S. Appl. No. 61/521,684, filed Aug. 9, 2011 for Johnson.
U.S. Appl. No. 61/525,125, filed Aug. 18, 2011 for Johnson.
U.S. Appl. No. 61/531,981, filed Sep. 7, 2011 for Johnson.
U.S. Appl. No. 61/549,158, filed on Oct. 19, 2011 for Johnson.
Non-Final Office Action for U.S. Appl. No. 13/103,874, mailed Aug. 1, 2014, 6 pages.
International Search Report and Written Opinion for International PCT Application No. PCT/US2014/043462, mailed Oct. 24, 2014, 16 pages.
Notice of Allowance for U.S. Appl. No. 13/103,874, mailed Nov. 13, 2014, 6 pages.
Non-Final Office Action for U.S. Appl. No. 13/801,919, mailed Nov. 19, 2014, 8 pages.
Notice of Allowance for U.S. Appl. No. 13/801,919, mailed Mar. 30, 2015, 5 pages.

* cited by examiner

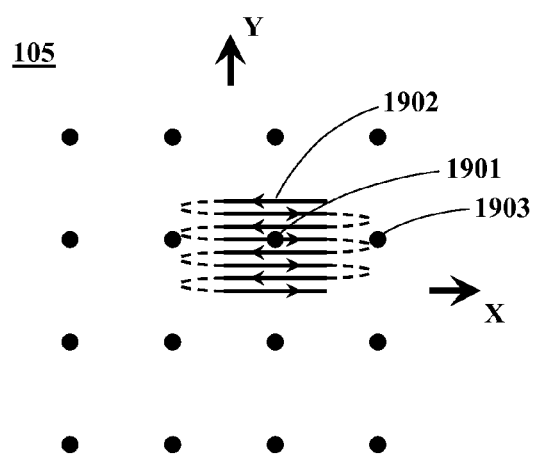
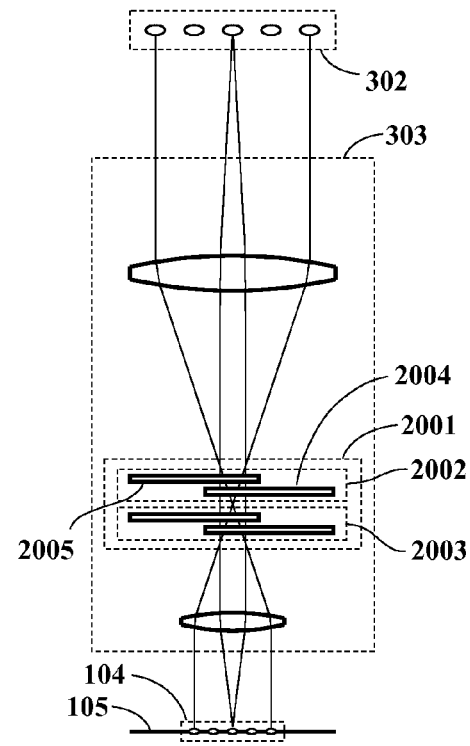
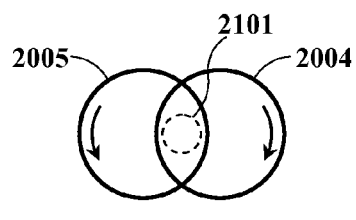
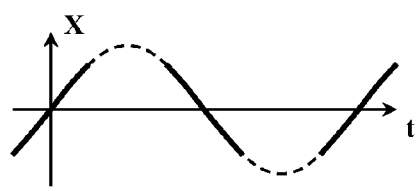
FIG. 19
FIG. 20
FIG. 21
FIG. 22

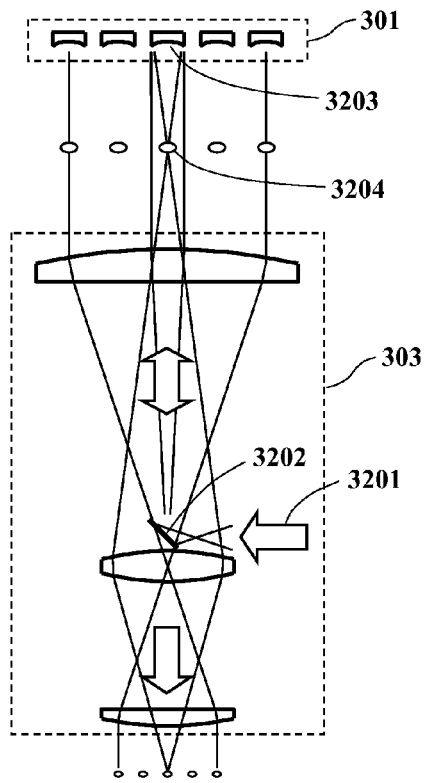
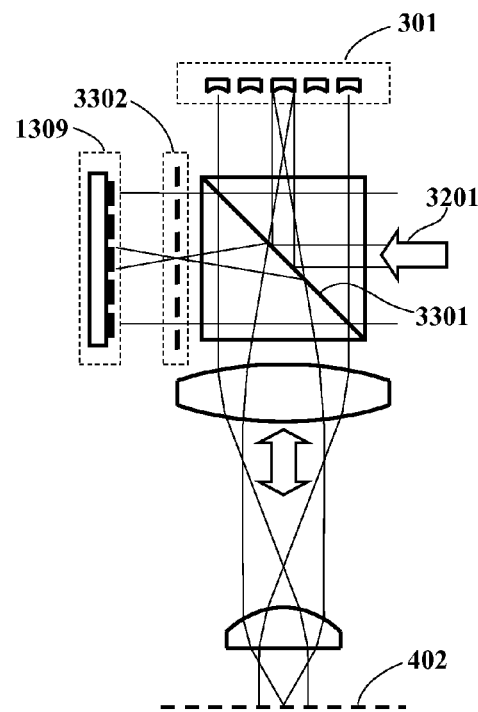
FIG. 32        FIG. 33
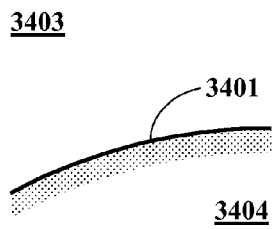
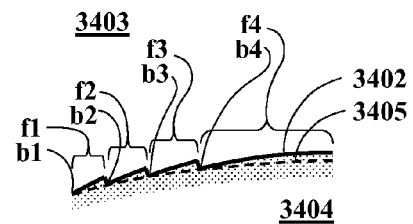
FIG. 34A        FIG. 34B

| | |
|---|---|
| $\Phi' = \Phi + C$ on the lens surface | 35.1 |
| $\Phi' = \Phi + jm2\pi + C$ on facet $j$ (at $m$-th order blaze wavelength) | 35.2 |
| $\Phi' = \Phi + jm2\pi + C$ on boundary $j$ (in $m$-th order, any wavelength) | 35.3 |
| $\Phi'_1 = \Phi_1 + jm2\pi + C_1$, $\Phi'_2 = \Phi_2 + jm2\pi + C_2$ on boundary $j$ | 35.4 |
| $\Phi'_1 - \Phi'_2 = \Phi_1 - \Phi_2 + C_1 - C_2$ on substrate | 35.5 |
| $\dfrac{\partial \Phi'}{\partial \lambda} = \dfrac{\partial \Phi}{\partial \lambda} + \dfrac{dC}{d\lambda}$ on substrate (at blaze wavelength) | 35.6 |
| $\Phi[\lambda, x, y] = 2\pi n[\lambda](x\sin[\theta[\lambda]] - y\cos[\theta[\lambda]])/\lambda + \Phi[\lambda, 0, 0]$ | 35.7 |
| $\Phi'[\lambda, x, y] = 2\pi n'[\lambda](x\sin[\theta'[\lambda]] - y\cos[\theta'[\lambda]])/\lambda + \Phi'[\lambda, 0, 0]$ | 35.8 |
| $\dfrac{\partial}{\partial \lambda}\Phi'[\lambda, x, y] - \dfrac{\partial}{\partial \lambda}\Phi[\lambda, x, y] - \dfrac{dC}{d\lambda} = 0$ $= 2\pi \left( \begin{array}{c} x\dfrac{d}{d\lambda}\left(\dfrac{n'[\lambda]\sin[\theta'[\lambda]] - n[\lambda]\sin[\theta[\lambda]]}{\lambda}\right) \\ -y\dfrac{d}{d\lambda}\left(\dfrac{n'[\lambda]\cos[\theta'[\lambda]] - n[\lambda]\cos[\theta[\lambda]]}{\lambda}\right) \end{array} \right) + (...)$ | 35.9 |
| $(x_j, y_j) = (x_0, y_0) + (jd, 0)$ | 35.10 |
| $\Phi'[\lambda, x_j, y_j] - \Phi[\lambda, x_j, y_j] - jm2\pi - C = 0$ $= j2\pi((n'[\lambda]\sin[\theta'[\lambda]] - n[\lambda]\sin[\theta[\lambda]])d/\lambda - m) + (...)$ | 35.11 |
| $n'[\lambda]\sin[\theta'[\lambda]] = n[\lambda]\sin[\theta[\lambda]] + m\lambda/d$ | 35.12 |
| $y = y_0 + (x - x_j)\tan[\alpha]$ on facet $j$ | 35.13 |
| $\Phi'[\lambda_B, x, y] - \Phi[\lambda_B, x, y] - jm2\pi - C = 0$ $= \dfrac{2\pi x}{\lambda_B \cos[\alpha]}(n'[\lambda_B]\sin[\theta'[\lambda_B] - \alpha] - n[\lambda_B]\sin[\theta[\lambda_B] - \alpha]) + (...)$ on facet $j$ | 35.14 |
| $n'[\lambda_B]\sin[\theta'[\lambda_B] - \alpha] = n[\lambda_B]\sin[\theta[\lambda_B] - \alpha]$ | 35.15 |
| $\alpha = \tan^{-1}\left[\dfrac{n'[\lambda_B]\sin[\theta'[\lambda_B]] - n[\lambda_B]\sin[\theta[\lambda_B]]}{n'[\lambda_B]\cos[\theta'[\lambda_B]] - n[\lambda_B]\cos[\theta[\lambda_B]]}\right]$ | 35.16 |
| $\theta = \theta' = \alpha = \sin^{-1}[m\lambda/(d(n'-n))]$ | 35.17 |

FIG. 35

| Transmission grating (FIG. 37A) | | |
|---|---|---|
| $d = 1.5\,\mu m,\ \theta = \theta' = \alpha = 20.8°$ | | |
| order ($m$) | TE eff. | TM eff. |
| -7 | 0.00050 | 0.000034 |
| -6 | 0.00055 | 0.0000087 |
| -5 | 0.00072 | 0.00053 |
| -4 | 0.0048 | 0.0031 |
| -3 | 0.010 | 0.0072 |
| -2 | 0.015 | 0.012 |
| -1 (blaze) | 0.80 | 0.80 |
| 0 | 0.014 | 0.014 |
| 1 | 0.018 | 0.019 |
| 2 | 0.024 | 0.028 |
| 3 | 0.035 | 0.047 |
| scatter | 0.12 | 0.13 |

| Reflection grating (FIG. 37B) | | |
|---|---|---|
| $d = 1.5\,\mu m,\ \theta = \theta' = \alpha = 5.1°$ | | |
| order ($m$) | TE eff. | TM eff. |
| -6 | 0.000083 | 0.00091 |
| -5 | 0.00022 | 0.00073 |
| -4 | 0.00040 | 0.00076 |
| -3 | 0.00069 | 0.00086 |
| -2 | 0.0012 | 0.0010 |
| -1 (blaze) | 0.86 | 0.90 |
| 0 | 0.0034 | 0.00156 |
| 1 | 0.0058 | 0.0019 |
| 2 | 0.0099 | 0.0023 |
| 3 | 0.016 | 0.0025 |
| 4 | 0.021 | 0.0026 |
| 5 | 0.0082 | 0.0020 |
| scatter | 0.067 | 0.017 |

| | |
|---|---|
| $\vec{E} = \hat{e}_1 E_1 + \hat{e}_2 E_2$ | 42.1 |
| $\vec{E}' = \hat{e}_1 E'_1 + \hat{e}_2 E'_2$ | 42.2 |
| $\begin{pmatrix} E'_1 \\ E'_2 \end{pmatrix} = \begin{pmatrix} \cos[\theta] & -\sin[\theta] \\ \sin[\theta] & \cos[\theta] \end{pmatrix} \begin{pmatrix} t_1 & 0 \\ 0 & t_2 \end{pmatrix} \begin{pmatrix} \cos[\theta] & \sin[\theta] \\ -\sin[\theta] & \cos[\theta] \end{pmatrix} \begin{pmatrix} E_1 \\ E_2 \end{pmatrix}$ | 42.3 |
| $P = E_1 / E_2$ | 42.4 |
| $P' = E'_1 / E'_2$ | 42.5 |
| $\rho = t_1 / t_2$ | 42.6 |
| $1 + \rho = (1 - \rho)\left(\cos[2\theta]\frac{P+P'}{P-P'} + \sin[2\theta]\frac{1-PP'}{P-P'}\right)$ | 42.7 |
| $\vec{E} = \hat{e}_1 + i\hat{e}_2,\ \vec{E}' = \hat{e}_2 \rightarrow P = -i,\ P' = 0,\ \rho = i\tan[\theta]$ | 42.8 |
| $2\pi r = N d / \cos[\theta]$ | 42.9 |
| $2\pi r = N d \sqrt{1+|\rho|^2}$ | 42.10 |
| $E'_1 = |E'_1|\exp[i\phi'_1]$ | 42.11 |
| $E'_2 = |E'_2|\exp[i\phi'_2]$ | 42.12 |
| $E'_1 = \sqrt{\frac{|E'_1|^2 + |E'_2|^2}{1+|E'_2/E'_1|^2}}\exp[i(\frac{1}{2}(\phi'_1+\phi'_2)+\frac{1}{2}(\phi'_1-\phi'_2))]$ | 42.13 |
| $E'_2 = \sqrt{\frac{|E'_1|^2 + |E'_2|^2}{1+|E'_1/E'_2|^2}}\exp[i(\frac{1}{2}(\phi'_1+\phi'_2)-\frac{1}{2}(\phi'_1-\phi'_2))]$ | 42.14 |
| $P' = |E'_1/E'_2|\exp[i(\phi'_1-\phi'_2)]$ | 42.15 |

FIG. 42

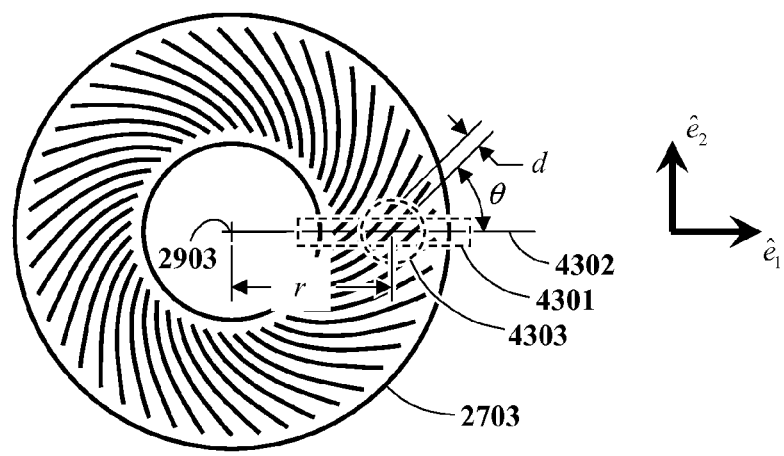

FIG. 43

| d (μm) | w / d | h (μm) | |ρ| | arg[ρ] | T | phase |
|---|---|---|---|---|---|---|
| 0.05000 | 0.3563 | 0.18091 | 0.9822 | 90.0° | 0.975 | -21.1° |
| 0.06000 | 0.3401 | 0.18224 | 0.9832 | 90.0° | 0.975 | -20.5° |
| 0.07000 | 0.3207 | 0.18403 | 0.9845 | 90.0° | 0.975 | -19.9° |
| 0.08000 | 0.2995 | 0.18614 | 0.9861 | 90.0° | 0.975 | -19.3° |
| 0.09000 | 0.2778 | 0.18848 | 0.9879 | 90.0° | 0.975 | -18.5° |
| 0.10000 | 0.2564 | 0.19097 | 0.9899 | 90.0° | 0.975 | -17.7° |
| 0.11000 | 0.2361 | 0.19353 | 0.9919 | 90.0° | 0.975 | -16.8° |
| 0.12000 | 0.2173 | 0.19607 | 0.9939 | 90.0° | 0.975 | -15.7° |
| 0.13000 | 0.1999 | 0.19850 | 0.9957 | 90.0° | 0.975 | -14.8° |
| 0.14000 | 0.1839 | 0.20091 | 0.9974 | 90.0° | 0.975 | -13.8° |
| 0.15000 | 0.1689 | 0.20361 | 0.9993 | 90.0° | 0.975 | -12.2° |

| $d$ (μm) | $w/d$ | $h$ (μm) | $|\rho|$ | $\arg[\rho]$ | $T$ | phase |
|---|---|---|---|---|---|---|
| 0.05000 | 0.5595 | 0.15819 | 0.9753 | 90.0° | 0.966 | -18.1° |
| 0.06000 | 0.5345 | 0.15938 | 0.9755 | 90.0° | 0.968 | -18.4° |
| 0.07000 | 0.5077 | 0.16018 | 0.9766 | 90.0° | 0.971 | -19.7° |
| 0.08000 | 0.4806 | 0.16048 | 0.9783 | 90.0° | 0.975 | -22.0° |
| 0.09000 | 0.4536 | 0.16020 | 0.9802 | 90.0° | 0.978 | -25.3° |
| 0.10000 | 0.4274 | 0.15930 | 0.9814 | 90.0° | 0.980 | -29.7° |
| 0.11000 | 0.4021 | 0.15776 | 0.9811 | 90.0° | 0.981 | -35.2° |
| 0.12000 | 0.3775 | 0.15551 | 0.9777 | 90.0° | 0.978 | -42.0° |
| 0.13000 | 0.3535 | 0.15236 | 0.9696 | 90.0° | 0.969 | -50.5° |
| 0.14000 | 0.3307 | 0.14784 | 0.9554 | 90.0° | 0.953 | -61.4° |
| 0.15000 | 0.3109 | 0.14075 | 0.9374 | 90.0° | 0.929 | -75.9° |
FIG. 46
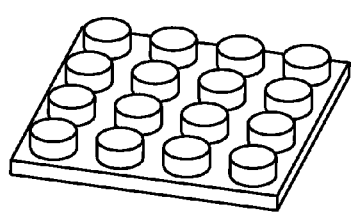
FIG. 47
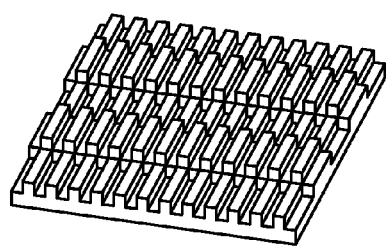
FIG. 48

SPOT-ARRAY IMAGING SYSTEM FOR MASKLESS LITHOGRAPHY AND PARALLEL CONFOCAL MICROSCOPY

CROSS-REFERENCE TO RELATED APPLICATIONS

This application claims the benefit under 35 U.S.C. §119 (e) of the following five applications, all of which name Kenneth C. Johnson as the inventor, and all of which are incorporated by reference in their entirety for all purposes:

U.S. Provisional Patent Application No. 61/498,427, filed Jun. 17, 2011 for "Scanned-Spot-Array Optical Lithography";

U.S. Provisional Patent Application No. 61/521,684, filed on Aug. 9, 2011 for "Scanned-Spot-Array Optical Lithography";

U.S. Provisional Patent Application No. 61/525,125, filed on Aug. 18, 2011 for "Spot-Array Imaging System for Maskless Lithography and Parallel Confocal Microscopy";

U.S. Provisional Patent Application No. 61/531,981, filed on Sep. 7, 2011 for "Spot-Array Imaging System for Maskless Lithography and Parallel Confocal Microscopy"; and U.S. Provisional Patent Application No. 61/549,158, filed Oct. 19, 2011 for "Spot-Array Imaging System for Maskless Lithography and Parallel Confocal Microscopy".

U.S. patent application Ser. No. 13/103,874, filed May 9, 2011 for "Optical Systems and Methods for Absorbance Modulation" (the '874 application), naming Kenneth C. Johnson as the inventor, is incorporated by reference in its entirety for all purposes.

BACKGROUND OF THE INVENTION

Scanned-Spot-Array Optical Lithography is a lithographic printing method in which an array of diffraction-limited focused-radiation spots is raster-scanned over a printing surface (a photosensitive optical recording medium) to synthesize a high-resolution recorded image. The spots may be individually modulated by a spatial light modulator. Systems of this type are described in U.S. Pat. No. 6,133,986, "Microlens Scanner for Microlithography and Wide-Field Confocal Microscopy" (hereafter the '986 patent), and in U.S. Pat. No. 6,897,941, "Optical Spot Grid Array Printer" (hereafter the '941 patent). Alternatively, the spots are not individually modulated, but are collectively modulated by a single modulator. A system of this type is described in the '986 patent.

A similar method can be employed in the context of Scanned-Spot-Array Optical Microscopy, wherein an array of focused-radiation illumination spots is raster-scanned over an inspection surface and the radiation reflected from (or transmitted through) the surface at each spot is collected and detected to construct a high-resolution raster image of the surface. Systems of this type are described in the '986 patent and in U.S. Pat. No. 6,639,201, "Spot Grid Array Imaging System" (hereafter the '201 patent).

The advantage of the scanned-spot-array method in the context of lithography is that it can provide high-throughput maskless printing capability, and it also eliminates optical proximity effects. In the context of microscopy, the method provides a capability for massively parallel confocal imaging.

An additional advantage of the method, in the approach described in the '986 patent, is that it can eliminate the need for wide-field, high-NA projection lenses, which account for much of the complexity and expense of conventional lithography and inspection microscopy systems. The systems described in the '986 patent use a comparatively low-NA projection lens in conjunction with an array of high-NA microlenses close to the printing or inspection surface. The microlenses need only achieve good on-axis point-imaging performance; there is no tolerance requirement on field flatness, distortion, or off-axis aberrations. Thus the microlenses should, in principle, be able to achieve imaging performance comparable to or better than state-of-the-art projection lenses. But it can be difficult to achieve this objective in practice because of the difficulty of forming small, high-NA microlenses to the requisite tolerances for diffraction-limited imaging.

By contrast, the systems described in the '941 and '201 patents separate the radiation into individual spots before it enters the projection lens, which images the spot array onto the printing or inspection surface at reduced magnification. (See the '941 patent at column 6, lines 53-56, and the '201 patent at column 7, lines 15-27.) The spots can be generated by a microlens array, but in this context the microlenses would be low-NA elements, and the spots may be filtered by an aperture array at the microlens focal plane. Low-NA microlenses could be fabricated more easily than the high-NA elements used in ' the '986 patent, and furthermore the spatial filtering would relax the microlens design requirements on aberration and scatter. But this approach requires a high-NA projection lens, which must meet stringent tolerance requirements on field flatness, distortion, and aberrations across a wide image field.

Thus, these two design alternatives involve a tradeoff. If the spots are generated by a microlens array close to the printing or inspection surface, then a very simple, low-NA projection lens can be used but the high-NA microlens design requirements are very challenging. If the spots are imaged through the projection optics, then they can be generated with comparatively simple, low-NA microlenses, but then the system requires a wide-field, high-NA projection lens meeting stringent diffraction-limited performance specifications.

SUMMARY OF THE INVENTION

The tradeoff between challenging microlens requirements and stringent projection lens requirements can be circumvented by employing micro-optics upstream of the projection lens to not only separate the radiation into discrete source spots, but to also compensate for imperfect imaging performance of the projection lens. This can be done in several ways: First, the source spots need not be focused through a common plane; they can be focused through a curved focal surface to compensate for any field curvature of the projection lens and ensure that the spot array is imaged onto a flat image plane. Second, the source spots need not be distributed on a uniform periodic grid; they can be distributed non-uniformly to compensate for image distortion of the projection lens so that the projected image of the spot array forms a uniform periodic grid. Third, the projection lens need not achieve stringent optical aberration tolerances because either the microlens array preceding the projection lens, or a separate phase-shift surface, can be configured to optimally correct the system's point-imaging performance for each individual spot. Both geometric and chromatic aberration can be corrected, and the spot-generation optics can be further configured to optimally control the radiation intensity and polarization across each individual spot beam.

A further understanding of the nature and advantages of the present invention may be realized by reference to the remain-

BRIEF DESCRIPTION OF THE DRAWINGS

FIG. 19 illustrates a bidirectional raster scan that would be employed with source scanning or beam scanning;

FIGS. 20, 21, and 22 illustrate the mechanics and operation of a beam-scanning system comprising counter-rotating Risley wedge disks;

FIG. 32 illustrates a projection lens that operates to direct illumination onto a reflective microlens array;

FIG. 33 illustrates a confocal microscope system in which the spot-generation optics comprise a micromirror array;

FIGS. 34A and 34B illustrate a conventional, refracting lens surface and a phase-Fresnel surface;

FIG. 35 tabulates equations relating to phase-Fresnel gratings and achromatization;

FIG. 42 tabulates equations relating to form-birefringent gratings and polarization control;

FIG. 43 illustrates geometric parameters of the polarization-control element of FIG. 29;

FIG. 46 tabulates design and optical performance data for a form-birefringent grating that is configured to minimize the grating height;

FIG. 47 illustrates a diffractive, zero-order attenuator that is configured to be polarization-neutral for normally-incident radiation; and FIG. 48 illustrates an optical surface that operates to control both polarization and zero-order intensity by means of crossed grating patterns.

DESCRIPTION OF SPECIFIC EMBODIMENTS

The Prior Art

Figure 1:
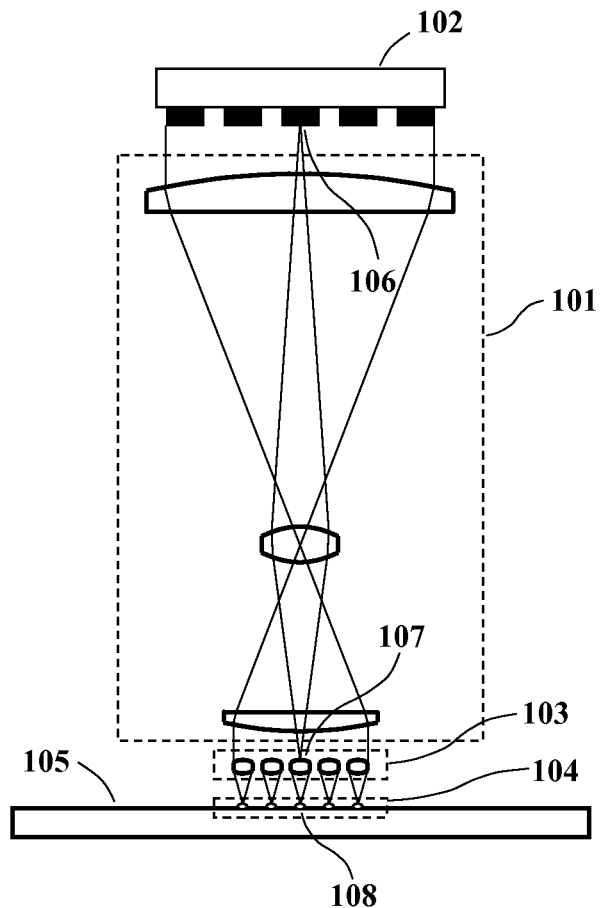
FIG. 1 illustrates a prior art lithography system.
Figure 2:
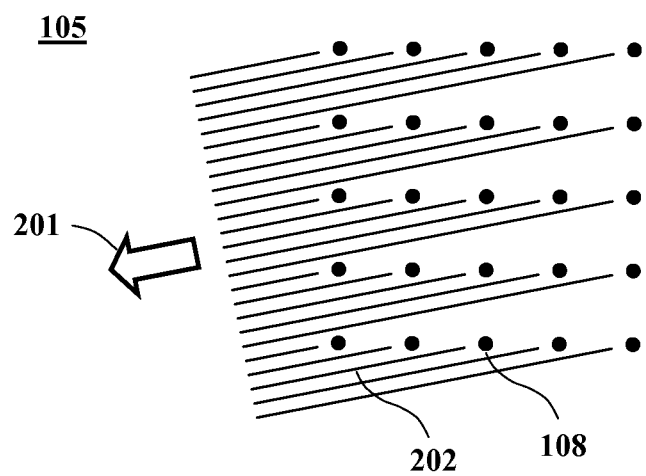
FIG. 2 illustrates how each focused spot traces a raster line across the surface as the spot intensity is modulated in synchronization with the scan in a system such as that shown in FIG. 1.
Figure 3:
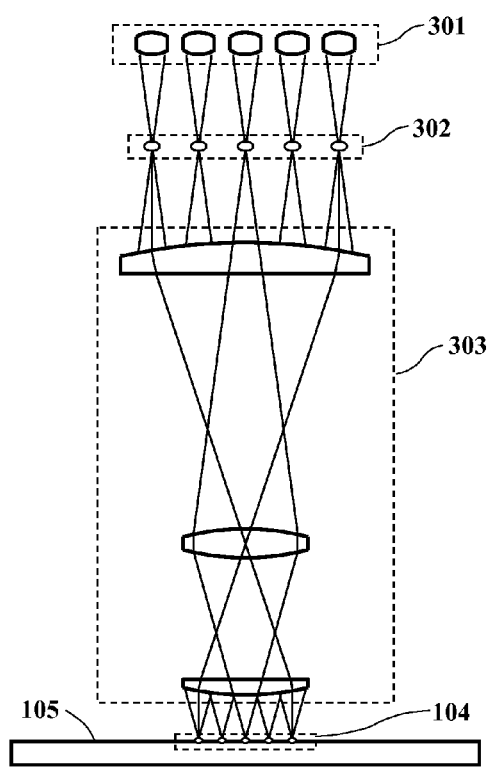
FIG. 3 illustrates a prior art approach for providing a microlens array with diffraction-limited performance and low light scatter.

To provide context for the description of the new invention, FIGS. 1-3 illustrate the prior-art systems discussed in the BACKGROUND OF THE INVENTION.

FIG. 1 illustrates a lithography system such as that described in the '986 patent, in which a projection lens 101 images a spatial light modulator (SLM) 102 onto a microlens array 103 at reduced magnification, and the microlenses focus the modulated radiation onto an array 104 of focused spots on a printing surface 105. Each modulator element such as element 106 is imaged onto a corresponding microlens such as element 107 so that the modulator element controls the radiation intensity at a corresponding focused spot 108. The surface 105 is raster-scanned in direction 201, as illustrated in FIG. 2, so that each focused spot 108 traces a raster line 202 across the surface as the spot intensity is modulated in synchronization with the scan.

The '986 patent mentions a variant of the FIG. 1 system in which there is no SLM, and the microlens array is uniformly illuminated with source-modulated illumination to print a periodic pattern having a periodicity matching that of the spot array. (See the '986 patent at column 11, line 57, to column 12, line 4.) Also, the '986 patent describes a confocal microscopy system that is similar to FIG. 1, except that the printing surface 105 is replaced by an inspection surface, there is no SLM, and the projection lens operates to both direct uniform illumination onto the microlens array and to collect radiation reflected from the inspection surface and direct it onto a detector array. Each detector element senses radiation from a corresponding focused spot as the surface is scanned, and the detector signals are processed to generate a high-resolution raster image of the surface.

The FIG. 1 system requires high-NA microlenses, which cannot be easily manufactured to achieve diffraction-limited performance with low light scatter, but this limitation is overcome by the approach discussed in the '941 and '201 patents, which is illustrated in FIG. 3. An array 301 of low-NA microlenses focuses radiation onto an array 302 of source spots at the object plane of projection lens 303, which images the source-spot array onto an array 104 of conjugate spot images on a printing surface (or inspection surface) 105 at the projection lens's image plane. A spot-delimiting aperture mask pattern (not shown) can be used to spatially filter the source spots at the microlens focal plane, so the microlenses need not achieve stringent scattering tolerances. In the context of lithography, an SLM (not shown) may be imaged onto the microlens array, as described in the '941 patent, so that the source spots are individually modulated. In the context of microscopy, the aperture mask pattern would operate as the pinhole array of a parallel confocal microscope.

Source Modulation

In an improvement over the prior art disclosed in the '941 patent, the source spots would not be individually modulated but would instead all be controlled by a single modulator at the radiation source. The system would be limited to printing periodic patterns matching the image spot array periodicity, but the data flow and data storage requirements would be reduced by several orders of magnitude relative to a system with individually modulated spots. This lithography method is a variant of a technique termed "Gratings of Regular Arrays and Trim Exposures" (GRATE), in which high-density circuit structures are formed initially as periodic patterns, and are then modified by non-critical trim exposures. But GRATE would be more limiting because the pattern period would typically be much smaller than the image spot period of the present invention. (GRATE is described by M. Fritze et al., Ref. 1)

Compensation for Field Curvature, Distortion, and Optical Aberration

Figure 4:
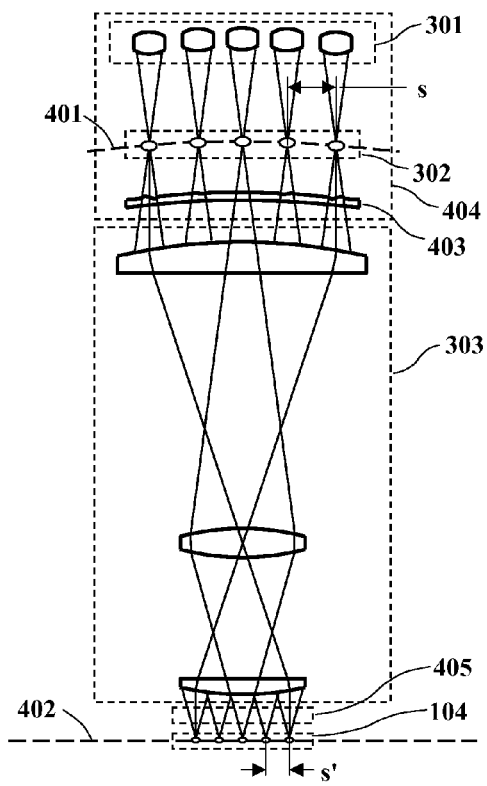
FIG. 4 illustrates apparatus incorporating techniques that allow the projection lens design requirements to be relaxed.

The system of FIG. 3 requires a high-NA, wide-field projection lens, but the lens design requirements can be relaxed by several methods illustrated in FIG. 4.

First, the projection lens need not achieve good flat-field imaging performance. It can have a curved object surface 401, and the source-spot array 302 can conform to the surface so that it is imaged onto a flat image plane 402 at the printing or inspection surface. (Alternatively, the source-spot array could be imaged onto an image surface having any desired field curvature; it need not be flat.)

Second, the projection lens need not achieve low-distortion imaging. The spacing s between source spots can vary non-uniformly across the spot array so that the spacing s' between the spot images is uniform across the image field, ensuring strict periodicity of the image-plane spots.

Third, the projection lens need not achieve stringent aberration tolerances, because an aberration-correcting device 403 can be placed in a region where the individual spot beams do not overlap, and can be configured to optimally correct the point-imaging performance for each individual spot. There are two such non-overlap regions, a region 404 in the object space, proximate the object surface, and another region 405 in the image space, proximate the image plane. (The individual spot beams are illustrated as light cones in FIG. 4.) An aberration corrector could be located in either or both regions, but the system would preferably use a single corrector in the object space. The aberration corrector cannot be at the source-spot array 302 (i.e., the spot beams are not in focus at the corrector), and it should preferably be as far from the source spots as possible within the non-overlap region. (In FIG. 4 the corrector is below the source-spot array, but it could alternatively be above the array, proximate the microlenses.)

The aberration corrector comprises a transmitting (or possibly reflecting) optical surface or surfaces whose topography is configured to induce an aberration-correcting phase shift in the transmitted radiation, and it may be formed either on the surface of a projection lens element or on a separate phase plate. (In FIG. 4 the corrector 403 is illustrated as slightly curved to conform to the curved object surface 401.) The corrector can be configured to compensate for aberrations in both the microlenses and the projection lens. Alternatively, the microlens surface shapes can be configured to compensate for the projection lens's aberration, eliminating the need for a separate aberration corrector.

Figure 5:
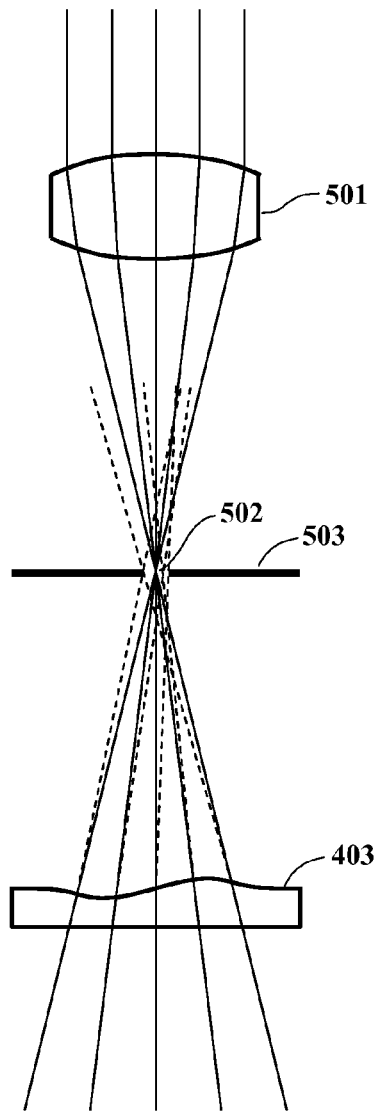
FIG. 5 is an expanded cross-sectional view of a portion of the FIG. 4 apparatus, showing a single microlens, and illustrating one embodiment of the aberration compensation method.

FIG. 5 is an expanded cross-sectional view of a portion of the FIG. 4 apparatus, showing a single microlens 501, and illustrating one embodiment of the aberration compensation method. The microlens 501 is configured to focus transmitted radiation to a diffraction-limited spot at focal point 502, which is filtered by an overfilled spot-delimiting aperture 503. (The point focusing is illustrated by five geometric rays passing through point 502, and the focal point should be at least approximately conjugate to the corresponding projected image point without aberration correction.) The aperture-filtered radiation is phase-shifted by aberration corrector 403 before entering the projection lens (not shown). The phase shift induces aberration in the transmitted beam, which counterbalances and nullifies the projection lens's aberration. The aberration is indicated by virtual rays traced back through the aperture, shown as dashed lines. The aberration corrector is configured so that the transmitted rays converge to a resolved image point after passing through the projection lens.

Figure 6:
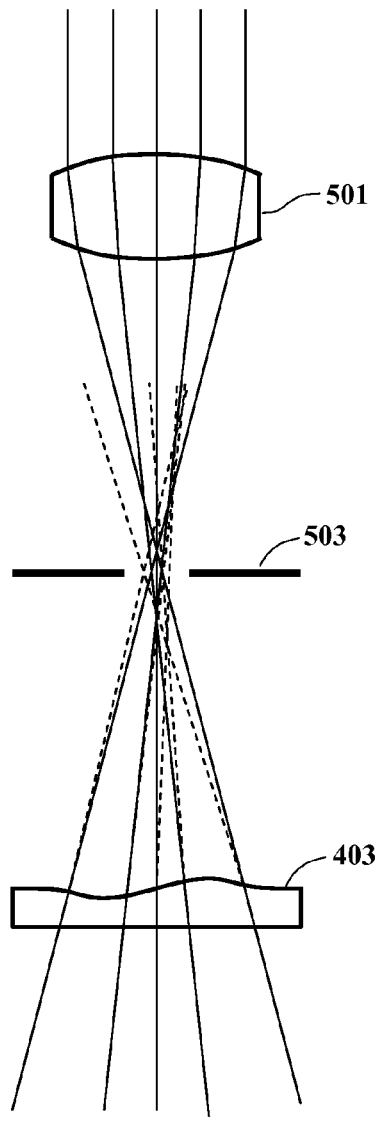
FIG. 6 illustrates an embodiment in which the aberration corrector compensates for aberration in both the microlenses and the projection lens.

FIG. 6 illustrates an embodiment in which the aberration corrector compensates for aberration in both the microlenses and the projection lens. In this illustration the microlens 501 generates a spherically-aberrated convergent beam, which passes through an underfilled aperture 503. The spherical aberration is indicated by the lack of a unique ray convergence point. (In this case the microlens focal point can be defined as the paraxial focal point, or as the point of maximum focused energy, which should be at least approximately conjugate to the corresponding projected image point without aberration correction.) The aperture 503 is larger than in the FIG. 5 configuration in order to accommodate the aberrated focused spot, and it only functions to block wide-field scattering. (For example, if diffractive zone-plate microlenses are employed, then aperture 503 would operate to pass the first diffraction order.)

Figure 7:
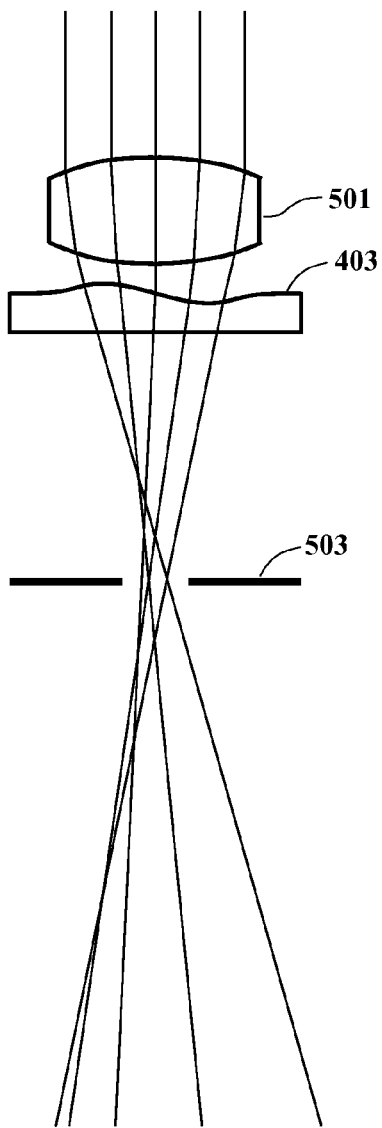
FIG. 7 illustrates an alternative to the FIG. 6 configuration where the aberration corrector is located immediately below the microlens array (between the microlenses and the focal points)
Figure 8:
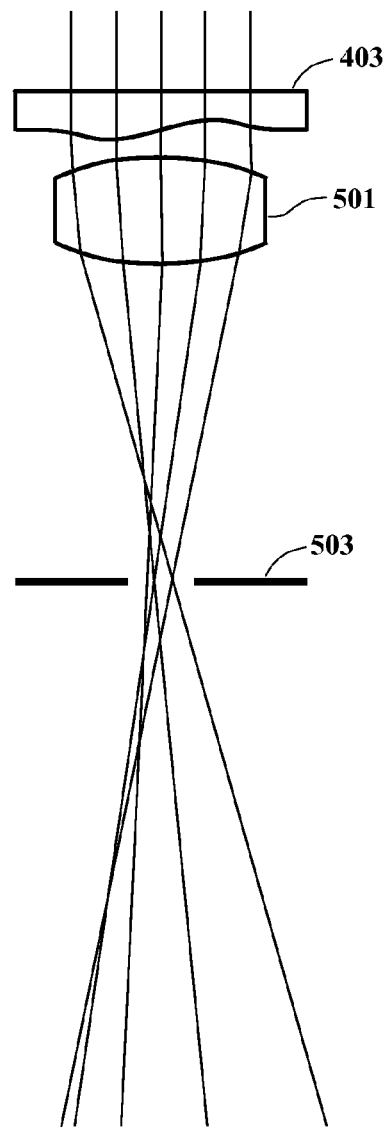
FIG. 8 illustrates a configuration where the aberration corrector precedes the microlenses in the light path.

As an alternative to the FIG. 6 configuration, the aberration corrector 403 could be located immediately below the microlens array (between the microlenses and the focal points), as illustrated in FIG. 7. It could also precede the microlenses in the light path, as illustrated in FIG. 8. The primary constraints on the corrector location are that distinct optical rays passing through the microlens 501 and projection lens to the target image point should not intersect on the aberration corrector, and rays traversing different microlenses should also not intersect on the corrector.

Figure 9:
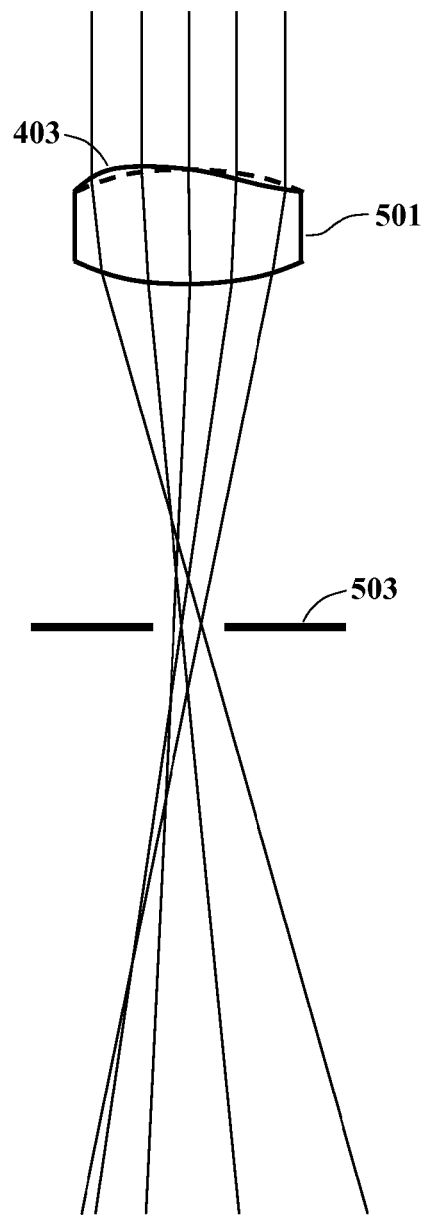
FIG. 9 illustrates a configuration where the microlenses themselves are configured to function as the aberration corrector.

The microlenses can themselves be configured to function as the aberration corrector, as illustrated in FIG. 9. In this illustration the dashed curve represents the microlens 501 surface form without aberration correction, and at least one lens surface deviates from this form to induce the desired corrective aberration. In the illustration, the aberration corrector 403 comprises the top microlens surfaces. If the microlens elements are diffractive zone-plate lenses, then the zone geometry can be configured to effect the aberration correction; there is no need to vary the surface height levels from a conventional, two-level planar zone-plate structure.

Figure 10:
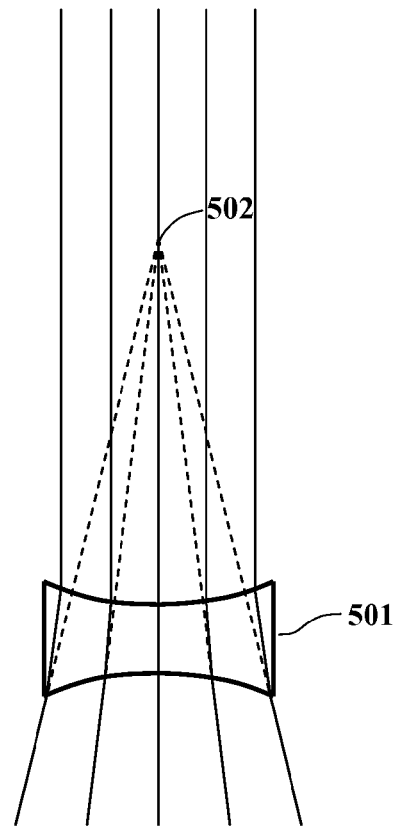
FIG. 10 illustrates a microlens that diverges the transmitted beam from a virtual focal point.

The spot-delimiting apertures 503 in FIGS. 5-9 are optional and may not be required if the microlenses have good optical quality. If the apertures are not required, then the system could employ diverging microlenses. FIG. 10 illustrates a microlens 501, which diverges the transmitted beam from a virtual focal point 502. The aberration corrector (not shown) could be positioned close to the microlens array or could be formed as a perturbation of the lens surface form (as in FIG. 9).

The aberration corrector may be combined with a optically absorbing layer whose thickness is determined to optimize each beam's intensity profile and to ensure a uniform intensity distribution across the image plane. (An embodiment with this feature will be illustrated in connection with EUV imaging.)

Optical Design

The source spots may be ill-defined because the microlenses may generate focused spots that are highly aberrated (FIG. 6), or because the aberration corrector intentionally induces a high degree of compensating aberration in the source spots (FIGS. 7-9). Furthermore, the source radiation would not pass through source spots if it is diverged by the microlenses (FIG. 10). But in any case, the radiation traversing the aberration corrector would comprise a discrete set of source beams, which are substantially non-overlapping and not in focus on the corrector. Each microlens transmits one of the source beams, and each beam is focused to a distinct diffraction-limited, image-plane spot after passing through the corrector and projection lens. The microlenses may function to partition incident illumination into corresponding discrete source beams or the illumination may be partitioned before intercepting the microlenses. (For example, the illumination may be partitioned by a SLM comprising discrete light-modulating pixel elements, which are imaged onto corresponding microlenses.) The positioning of the aberration corrector is selected so that the individual beams intercept the corrector over separate areal regions that are preferably large, but are substantially non-overlapping.

Each source beam is characterized by a uniquely-defined optical phase function, which is defined over the spatial region traversed by the beam. Constant-phase surfaces define geometric waves. The waves propagate through the optical system according to the laws of geometric optics, originating from a radiation source (e.g., a laser source) and converging on the target image point. Optical rays are perpendicular to the geometric waves, and the optical phase at any location can be determined by ray tracing from either a focal point or a wave of known phase. The geometric phase may be undetermined at an intermediate focal point or at an optical caustic where rays cross, but the position of the aberration corrector should be chosen so that there are no ray crossings on the corrector.

The portion of the aberration corrector traversed by any particular source beam defines a corrector element, which is configured to achieve precise, aberration-free point imaging of the traversing beam. This can be achieved as follows: The optical phase in the spatial region immediately preceding the corrector element in the optical path is defined by ray tracing from the radiation source through any optical elements preceding the corrector element. The optical phase in the region immediately following the corrector element is similarly defined by reverse ray tracing from the target image point back through the projection lens and any other intervening optics. Rays intercepting either the corresponding microlens aperture boundary or any limiting aperture boundary in the projection lens will delimit the corrector element's aperture extent. (The microlens may either precede or follow the corrector element in the optical path.) Within this aperture region, the corrector element is defined according to a phase-matching condition: The optical phase from the radiation source to any point on the corrector element, plus the optical phase from that point to the image point, should be constant across the element.

The ray tracing procedure can be applied to refractive or reflective surfaces, and to diffractive surfaces such as zone-plate lenses and phase-Fresnel surfaces (which can be either refractive or reflective). The optical phase difference (in radians) between any two points on a ray is determined by summing the optical path length (physical length times refractive index) along the ray segments, and multiplying by $2\pi/\lambda$ (where $\lambda$ is the vacuum wavelength). In addition, phase discontinuities across diffractive elements must be included in the phase calculation. For a zone-plate lens or phase-Fresnel lens, the phase discontinuity across the lens surface is $2\pi$ times a "zone number," which is a continuous function of position over the surface that varies by one unit per grating cycle. (This assumes that the first diffraction order is used; if the m-th order is used, then the multiplier is $2\pi m$.)

The aberration corrector elements could also be designed as phase-Fresnel surfaces to limit their height profile. Appendix B in the '874 application describes a methodology for designing phase-Fresnel surfaces based on the above-described phase matching criterion.

The above-described geometric-optics design procedure may suffice to determine the aberration corrector design with adequate accuracy, but in some cases the design may need to be refined by applying a physical-optics model of wave propagation through the system, including a realistic vector-wave simulation of diffractive surface structures.

Even without an aberration corrector, the positioning of the microlenses can be chosen to at least nullify field curvature and image distortion at the image plane. This can be done by reverse ray tracing a bundle of rays from each target image point through the projection lens and determining approximately where the rays converge. The convergence locus may be highly aberrated and ill-defined, but the approximate point where the ray density is maximum could define the location of a microlens focal point conjugate to the image point. After the microlens focal point positions are defined and the microlenses are designed, the aberration corrector is designed by the above-described procedure to nullify the aberration. (If the microlens surfaces themselves perform the aberration-correction function, then a preliminary microlens layout can be initially defined using point-focus elements, after which the microlens surface geometry is modified to effect aberration correction.)

Optical Fabrication

The aberration corrector's surface shape can be formed by a method such as ion milling or gray-scale lithography. For optimum performance, the point-imaging performance of both the projection lens and the microlens array can be interferometrically tested, and the corrector design can be adjusted to compensate for measured optical aberrations. An additional interferometric metrology step could be applied to the fully assembled system, and an additional etch process could be applied to the corrector surface to eliminate any residual aberrations.

Figure 15:
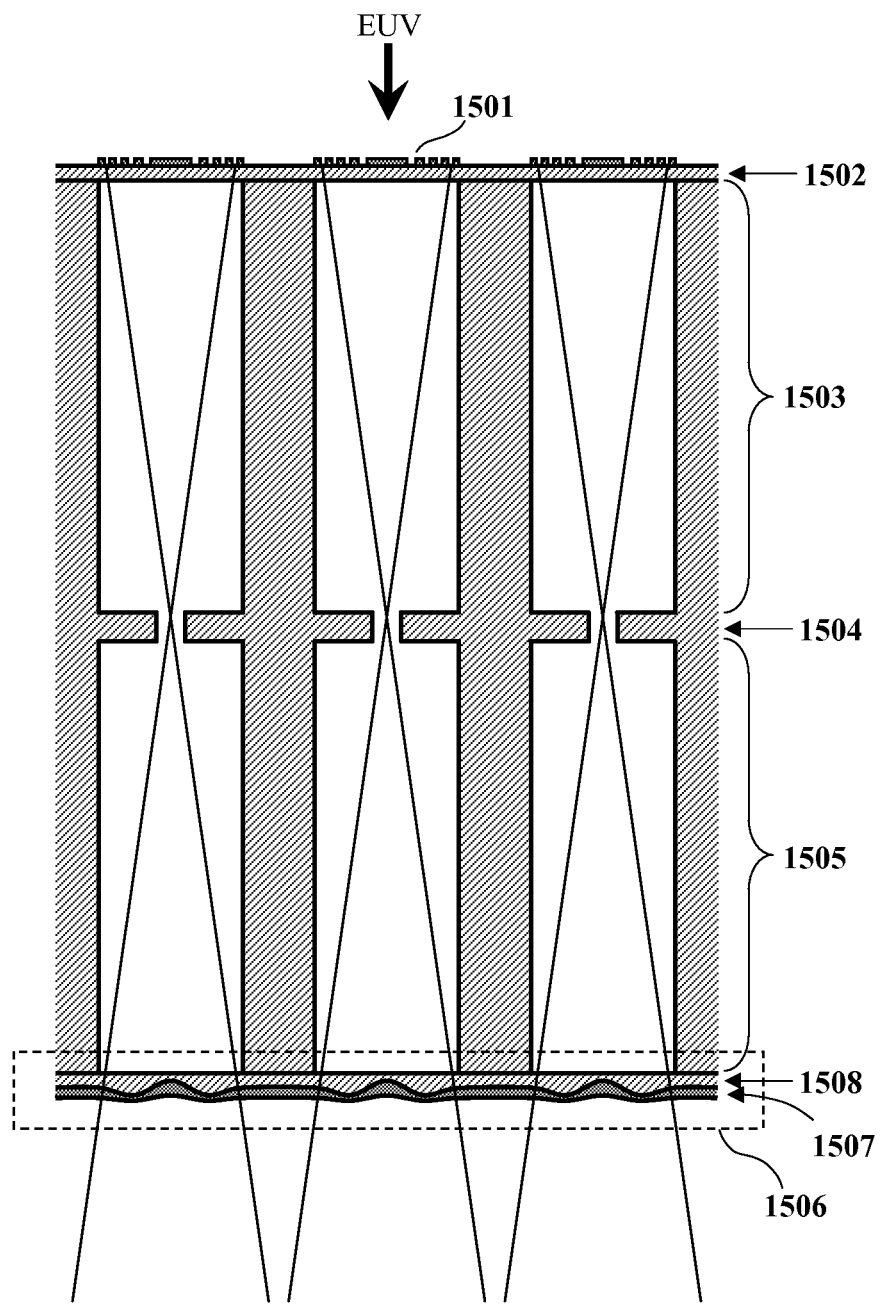
FIG. 15 is a cross-section view of EUV spot-generation optics comprising microlenses formed as molybdenum zone-plate lenses and aberration correctors formed as silicon/molybdenum contoured layers.
Figure 16:
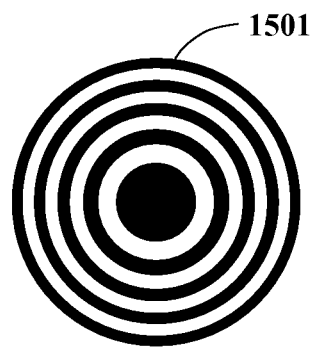
FIGS. 16 and 17 are plan views that illustrate alternative embodiments of the microlenses shown in FIG. 15.
Figure 17:
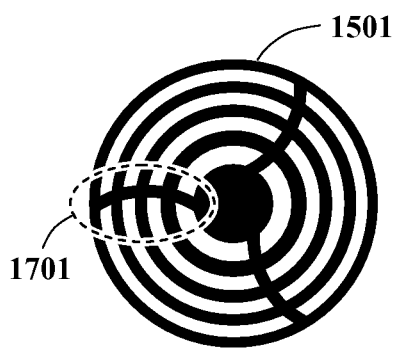

The lens-corrector assembly can be used to lithographically pattern the spot-delimiting apertures in a self-aligned process wherein a focused-spot array originating from the image plane is projected through the optics to expose a photoresist at the object surface. The assembled lens, corrector, and aperture array could also be used to form the microlenses in a similar self-aligned process. For example, the spot array can be projected from the image plane through the projection system, aberration corrector, and spot-delimiting apertures to lithographically pattern the microlens array, either in a single gray-scale etch step, or preferably by means of a pattern-transfer technique such as that discussed in the '986 patent (column 12, line 8 to column 13, line 33; FIGS. 15-17). The pattern-transfer method has the advantage that it provides accurate control over the microlens surface shape.

Zone-plate lenses can be formed by a process such as e-beam lithography or focused-ion-beam machining Such lenses cannot be post-processed to fine-adjust the transmitted beam's phase profile, but an aberration-correcting zone plate lens could be used in series with a much weaker phase-plate aberration corrector, which can be surface-machined to correct residual phase errors.

Dual-Wavelength Lithography/Imaging System

The above-described spot-array imaging system could be especially useful for a dual-wavelength system that uses a particular exposure wavelength for lithographic printing, and simultaneously uses another wavelength for confocal imaging to provide real-time positional feedback information during the printing process. For example, a DUV wavelength could be used to expose a photoresist while a 633 nm imaging wavelength is used to track focus and overlay alignment.

Figure 11:
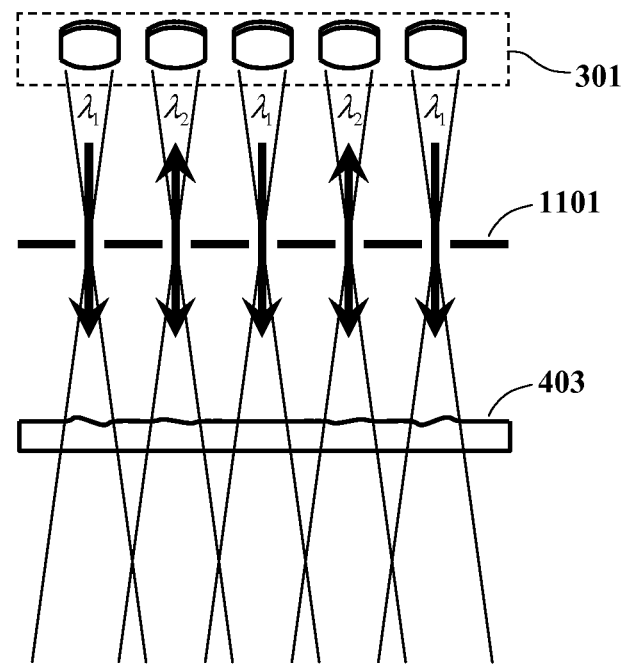
FIG. 11 illustrates a portion of the microlens array, spot-delimiting aperture array, and aberration corrector plate in cross-section configured to effect dual-wavelength operation.
Figure 12:
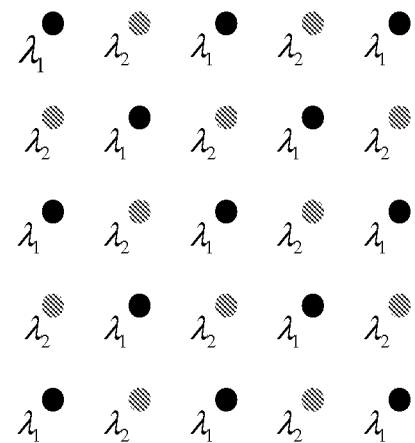
FIG. 12 is a plan view that illustrates a checkerboard-type pattern of image-plane spots resulting when microlenses configured to transmit different wavelengths are interleaved.

One way to effect dual-wavelength operation is illustrated in FIG. 11, which shows a portion of the microlens array 301, spot-delimiting aperture array 1101, and aberration corrector plate 403 in cross-section. The microlenses have wavelength-selective reflective coatings on their top surfaces, which allow either the exposure wavelength $\lambda_1$ or imaging wavelength $\lambda_2$ to transmit through each microlens. The $\lambda_1$-transmitting and $\lambda_2$-transmitting microlenses are interleaved so that the image-plane spots form a checkerboard-type pattern such as that illustrated in FIG. 12 in plan view. (The dots represent focused spots, and the spot wavelengths are indicated in the figure.) The projection lens can be at least approximately achromatized to match the $\lambda_1$ and $\lambda_2$ magnifications by means such as a two-glass achromat or a phase-Fresnel lens surface, and the aberration corrector can neutralize any residual chromatic aberration.

Figure 13:
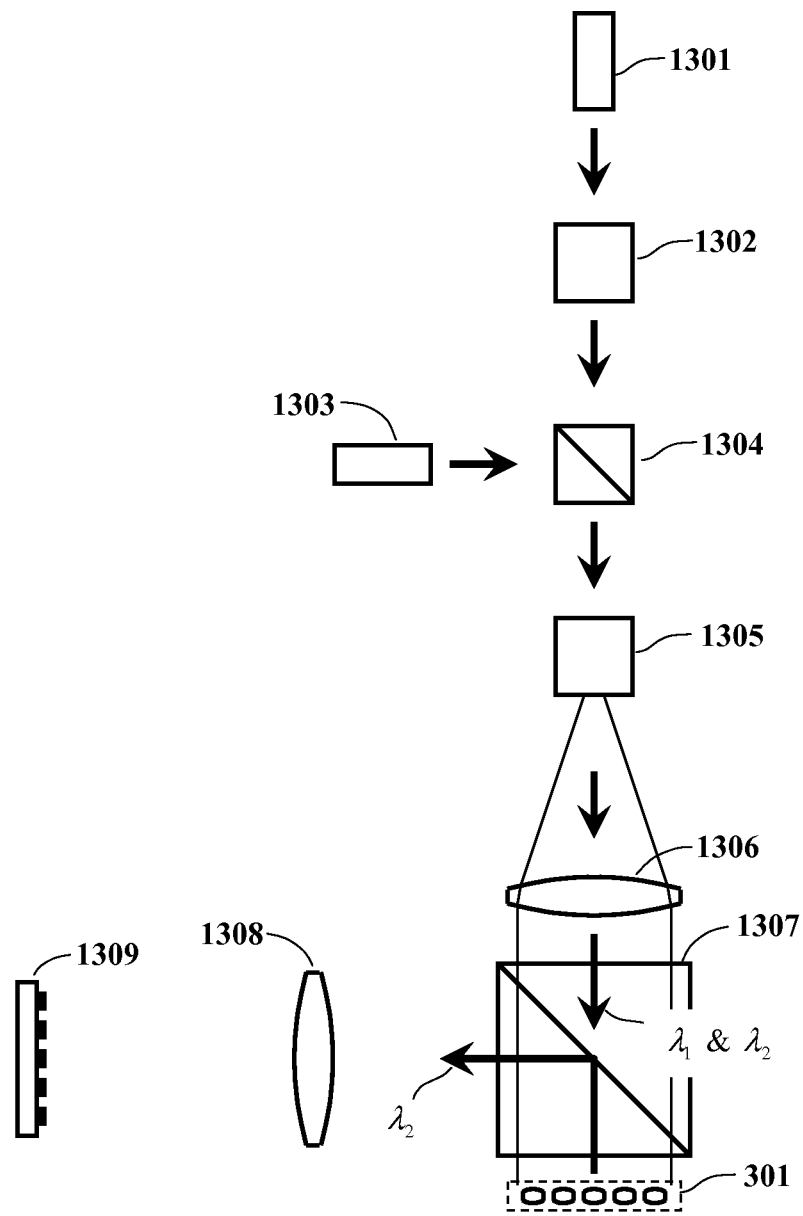
FIG. 13 illustrates a dual-wavelength system such as that of FIGS. 11 and 12 in which one set of microlenses is used to both transmit illumination to the printing surface, and collect reflected radiation from the surface for confocal image acquisition.

The $\lambda_2$-transmitting microlenses would be used to both transmit illumination to the printing surface, and collect reflected radiation from the surface, in a confocal imaging system such as that illustrated schematically in FIG. 13. A first laser source 1301 generates $\lambda_1$ radiation, which is modulated by modulator 1302; and a second laser source 1303 generates $\lambda_2$ radiation, which is combined with the modulated $\lambda_1$ radiation by means of a dichroic beam combiner 1304. (This system uses source modulation, but it could alternatively be adapted to use an SLM in the $\lambda_1$ optical path, as in the '941 patent.) The combined $\lambda_1$ and $\lambda_2$ radiation is expanded by beam expander 1305 and collimated by collimator 1306, and transmits through the microlens array 301 and projection system (not shown) and onto the printing surface. (The microlenses selectively transmit $\lambda_1$ or $\lambda_2$, as illustrated in FIG. 11.) The $\lambda_2$ radiation reflected from the printing surface is collected by the projection system and microlens array, is separated out of the illumination light path by beam splitter 1307, and is directed through imaging lens 1308 and onto detector array 1309. Lens 1308 images each microlens onto a corresponding detector element, which senses the confocal signal from a particular corresponding $\lambda_2$ image point on the printing surface.

The confocal signal has maximal focus sensitivity in a slightly out-of-focus condition, so it would be advantageous to design the aberration corrector to induce a small focus shift in selected $\lambda_2$ spots. Selected pairs of proximate spots can be focus-shifted in opposite directions, and the aberration corrector can be further configured to laterally shift each such pair so that the two spots trace the exact same raster line. A comparison of the two confocal signals from each pair, acquired as they traverse the same raster line at the two focus heights, would provide an accurate, signed measure of focus error.

Figure 14:
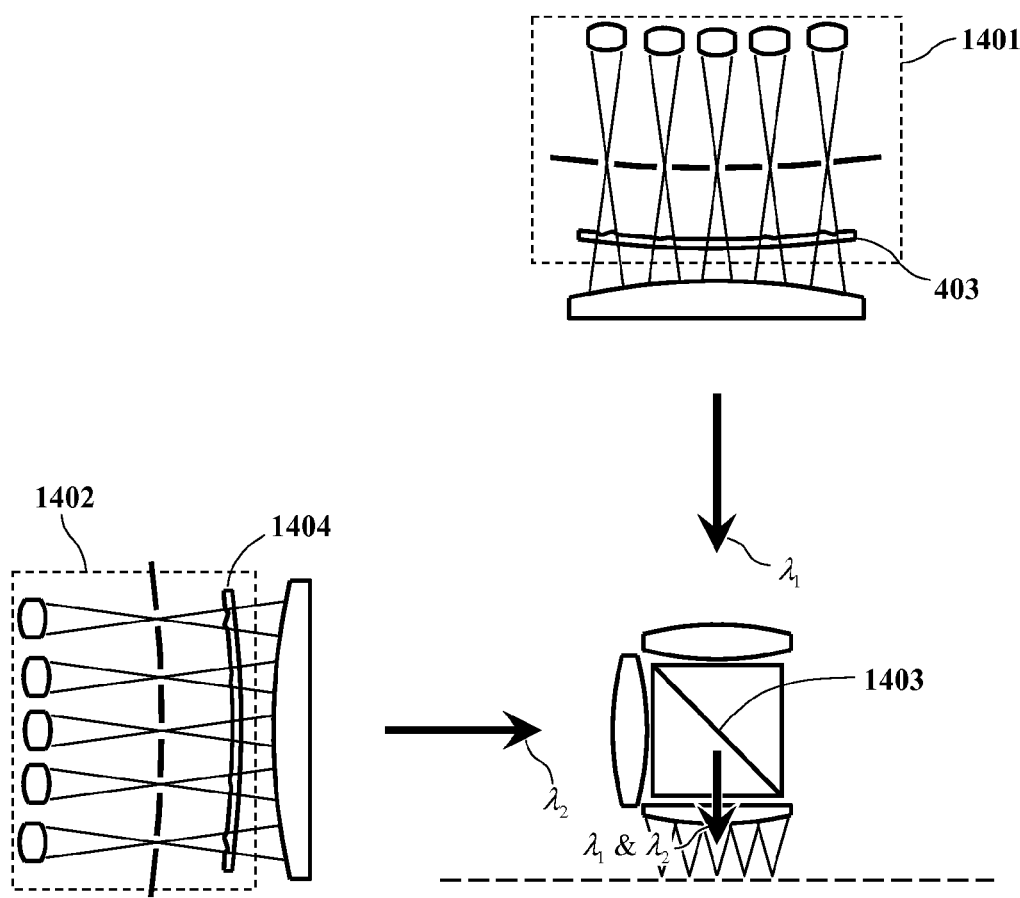
FIG. 14 illustrates an alternative dual-wavelength system in which the two wavelengths are combined in the projection optics.
Figure 28:
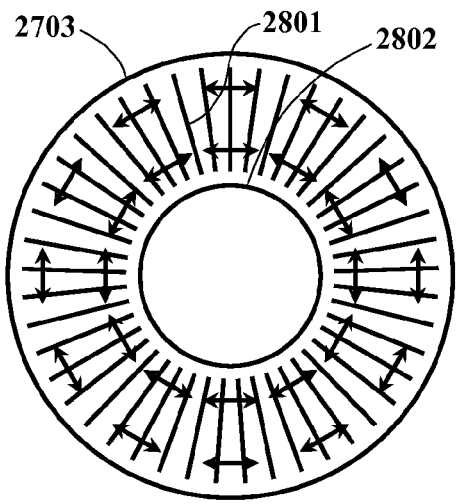
FIG. 28 illustrates one type of aperture polarization-control element, a radial wire-grid polarizer, in plan view.

In an alternative approach, the two wavelengths could be combined in the projection optics, as illustrated in FIG. 14. Two sets of spot-generation optics such as that of FIG. 4 are provided, a first set 1401 for the exposure wavelength $\lambda_1$ and a second set 1402 for the imaging wavelength $\lambda_2$, and the two wavelengths are merged by a dichroic beam combiner 1403 within the projection optics. (Alternatively, the system could use an aperture-division beam combiner such as that illustrated in FIG. 28 of the '874 application.) Each set of spot-generation optics includes a microlens array, a spot-delimiting aperture array, and an aberration corrector as described previously. The $\lambda_2$ optics would be used to both direct the $\lambda_2$ spot array onto the printing surface and also collect the reflected $\lambda_2$ radiation and direct it onto a detector array (not shown).

AMOL Embodiment

A dual-wavelength optical system such as that illustrated in FIG. 14 could also be useful for Absorbance Modulation Optical Lithography (AMOL), wherein the second wavelength $\lambda_2$ is not used for imaging, but is used to induce absorbance in a photochromic layer on the printing surface. The $\lambda_2$ focused spots on the image plane would coincide with the $\lambda_1$ focused spots, and the $\lambda_2$-transmitting optical elements would be configured to induce an optical null at the center of each $\lambda_2$ spot to create a sub-wavelength transmittance aperture in the photochromic layer through which the $\lambda_1$ radiation transmits. A similar system is described in the '874 application. (See FIG. 1 in the '874 application.) The '874 application describes several methods for inducing the optical null, which would be applicable in the present context.

The FIG. 14 system incorporates aberration correctors 403 and 1404 for wavelengths $\lambda_1$ and $\lambda_2$, respectively, which are configured to optimize the projection system's point-imaging performance for each individual focus spot. The $\lambda_2$ corrector 1404 can be further configured to induce the optical nulls by superimposing a spiral-phase pattern (either stepped or continuous) on the aberration-correcting phase pattern. Such patterns are illustrated in FIGS. 18 and 20 in the '874 application. As noted previously, the microlens surfaces can be configured to operate as the aberration corrector, and the same surfaces can incorporate a spiral-phase pattern as illustrated in FIGS. 19 and 21 in the '874 application. If the microlenses are diffractive, zone-plate lenses, then the zone pattern can be configured to both effect aberration correction and incorporate the spiral-phase pattern. (Spiral-phase, zone-plate structures are described by H-Y. Tsai et al., Ref. 2.)

The system could be further configured to provide both imaging and absorbance modulation capability, for example, by using a system such as that of FIG. 13 to merge exposure and imaging wavelengths into the optical path, and also using the FIG. 14 system to merge a masking wavelength with the exposure and imaging wavelengths.

EUV Embodiment

FIGS. 1, 3 and 4 illustrate the projection lens schematically as a dioptric (refractive) system, but it could more generally comprise a catoptric (reflective) or catadioptric (refractive and reflective) system. (The term "lens" is used generically to denote refractive and/or reflective imaging systems.) In particular, the invention would be applicable to extreme ultraviolet (EUV) lithography systems in which the projection optics consist only of mirrors. FIG. 15 illustrates a possible design configuration for EUV spot-generation optics, in cross-section. This particular embodiment could operate at a wavelength of 13.5 nm.

The EUV microlenses are molybdenum (Mo) zone-plate lenses such as lens 1501, shown in cross-section in FIG. 15 and in plan view in FIG. 16 or FIG. 17. The lenses are supported on a thin silicon (Si) substrate 1502, which is formed on top of a microchannel plate 1503. The lens form for this embodiment is illustrated in FIG. 16. Alternatively, the Si substrate can be omitted, and free-standing zone-plate lenses can be attached directly to the microchannel plate. In this case, the zone rings could be held in place by spider vanes, as illustrated in FIG. 17. (The vanes, such as vane 1701, are preferably curved to avoid azimuthal concentration of the radiation diffraction by the vanes.)

Each zone-plate lens focuses EUV radiation through a microchannel and through a spot-delimiting aperture in an aperture array 1504. The aperture-filtered beam then passes through a channel in a second microchannel plate 1505, and through an aberration-corrector plate 1506 comprising two surface-contoured layers, a Mo layer 1507 and a Si layer 1508. The Mo layer's surface topography controls the phase distribution of the transmitted beam. The Si layer's surface topography is determined to compensate for the Mo layer's thickness-dependent absorption, so that the two layers in combination exhibit uniform transmittance intensity. The Si layer thickness can also be optimized to control the image spot's intensity level and ensure a uniform exposure dose over the full printing field.

Rather than using a separate aberration corrector 1506, the zone-plate lenses can be designed to induce the desired aberration-correcting phase pattern. Alternatively, the system could use continuous-profile, refracting EUV microlenses, or phase-Fresnel microlenses, rather than zone-plate microlenses, and the surface geometry of such elements could also be configured to perform the aberration-correction function. (Continuous-profile EUV microlens structures are described in U.S. Pat. Nos. 6,498,685 and 7,116,405.) A two-layer Mo/Si microlens structure can be used to optimally control both the phase and intensity profile of the transmitted beam and to ensure a uniform image-plane intensity distribution. For optimum performance, the projection optics' imaging performance and transmitted intensity distribution should be tested, and the fabrication of the microlenses and aberration corrector should be tailored for the as-built projection system.

The source-spot array would replace the reflective photomask in a conventional EUV system. The spots could be modulated by means of high-speed micromechanical shutters integrated with the aperture array 1504, but in a simpler embodiment the EUV illumination would be source-modulated and the system would print periodic patterns. (Alternatively, an integrated shutter array could be employed to provide intermittent masking of selected spots, but it would not need to operate at a high switching speed and would not limit printing throughput.) Source modulation could be effected with a laser-produced plasma source by modulating the laser. (The laser repetition rate would limit throughput.)

Aside from the advantage of maskless operation, the aberration-correcting capability of this system could significantly relax the optical performance requirements of the optical projection system. This could make it possible to increase the projection system's numerical aperture and improve print resolution. Alternatively, the required number of EUV mirrors could be reduced, resulting in relaxed tolerances on surface figure and mirror coating matching, and also reducing source power requirements. A two-mirror Schwarzschild or Cassegrain mirror configuration could perhaps be adapted for high-NA operation with aberration correction. (A similar configuration is described in U.S. Pat. No. 6,331,710.)

The Radiation Source

Scanned-spot-array lithography requires a continuous or high-repetition-rate radiation source to achieve high printing throughput. EUV lithography uses pulsed radiation sources such as laser-produced plasma sources, which operate at frequencies of only up to about 500 KHz. (See D. C. Brandt et al., Ref 3.) The moderate repetition rate would limit throughput, but it would also limit source power requirements. Thus, the low throughput might be offset by the lower cost of the source, plus the advantages of maskless operation and aberration correction.

For DUV lithography using excimer lasers, the repetition-rate limitation is more constraining. Laser sources for 193-nm lithography typically have repetition rates no higher than 6 kHz. However, it may be possible to multiplex the output from a number of comparatively low-power, synchronized lasers to generate a combined output with much higher power and repetition rate.

The choice of laser sources is less limited at longer wavelengths. For example, Coherent, Inc. produces a 266-nm "quasi-continuous-wave" laser operating at 120 MHz. (The power rating is currently only 500 mW, but could potentially be increased to the 6-10 W range at a lower frequency.) Optical resolution with 266 nm would not be as good as at 193 nm, but could be improved by using a "solid immersion" technique, which will be discussed below. The choice of solid immersion materials is less limiting at longer wavelengths, and a 266-nm system using a solid immersion lens with a refractive index of 2 would have optical resolution comparable to 193 nm with water immersion (index 1.44). Furthermore, with multiple patterning the print resolution is fundamentally limited by overlay, focus, and exposure control, and not by wavelength. So even without solid immersion it may be possible to achieve print feature densities with a 266 nm source comparable to 193-nm lithography.

Aberration Corrector with Narrow-Band Achromatization

The aberration corrector would typically comprise a surface relief pattern on a transmitting optical surface, which could be either a microlens surface or a separate phase-plate surface. As noted previously, the aberration corrector elements could also be designed as phase-Fresnel surfaces to limit their height profile. Alternatively, a lithography system could employ phase-Fresnel corrector elements to achieve narrow-band achromatization at the exposure wavelength. This could eliminate the need for laser line narrowing, resulting in higher and more stable power output.

This use of phase-Fresnel surfaces differs from other applications that relate to achromatization between two widely-separated wavelengths. For this application, the two design wavelengths are nearly coincident, and the phase-Fresnel surface operates to make the system's point-imaging performance insensitive to wavelength within a narrow range of source wavelengths. Since the source spectrum is fairly narrow, the phase-Fresnel structures can be blazed to achieve high diffraction efficiency over the full spectrum.

The phase-Fresnel structure would be configured to correct and nullify chromatic aberration throughout the projection system and in the microlenses. (The phase-matching design method described in Appendix B of the '874 application can be used to design the corrector elements.) With this facility, the aberration corrector can be configured to substantially eliminate chromatic, as well as geometric, point-imaging aberration in the optical system. The only fundamental aberration constraint on the projection lens is that the uncorrected aberration point spread (both geometric and chromatic) at the image plane should be small in relation to the image spot separation.

Geometric and chromatic aberration can be individually corrected for each source spot by means of a single optical surface, or the two aberration types could be corrected by separate optical surfaces in series. For example, in the FIG. 8 embodiment element 403 could use a phase-Fresnel surface to correct both geometric and chromatic aberration, or it could be configured to only perform geometric aberration correction while a phase-Fresnel surface on microlens 501 corrects chromatic aberration.

Source-Spot Micro-positioning Control

Figure 18A:
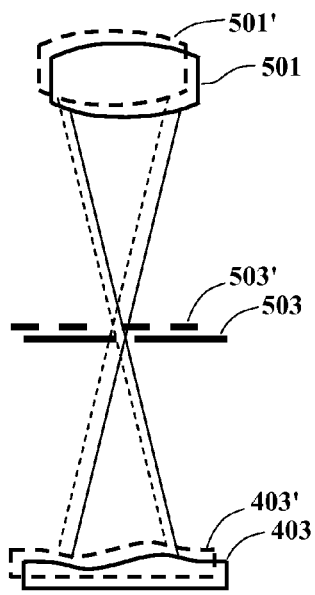
FIGS. 18A-18F illustrate positional displacements of the spot-generation optics in response to source-spot micro-positioning control.
Figure 18B:
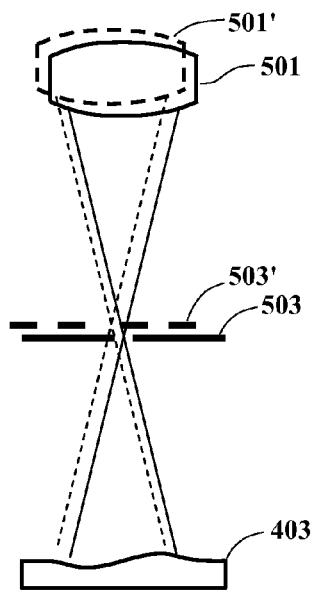
Figure 18C:
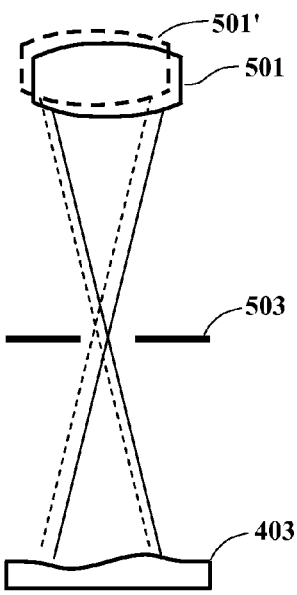
Figure 18D:
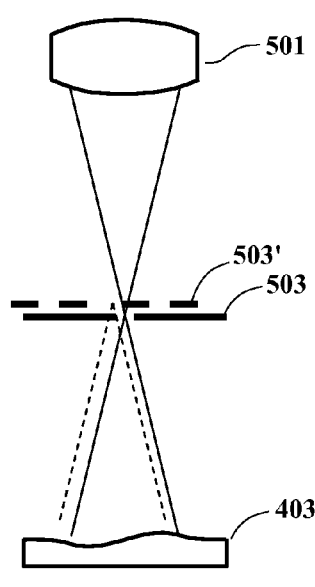
Figure 18E:
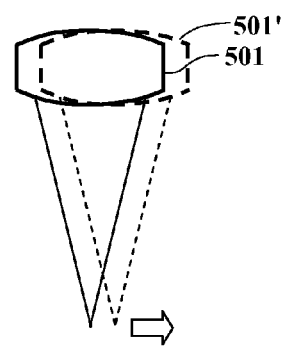

In some embodiments of the invention it may be advantageous to equip the spot-generation optics with means for independently moving each individual source spot over a small positional range. This could be achieved by attaching the microlens, spot-delimiting aperture, and aberration corrector subassembly associated with each source spot to a MEMS-actuated positional control mechanism. For example, FIG. 18A illustrates microlens 501, aperture 503, and aberration corrector element 403 being moved incrementally, as a unit, to a displaced position indicated by the dashed lines. (The displaced elements are indicated as 501', 503' and 403'.) For small displacements, it may suffice to actuate only the microlenses and apertures (FIG. 18B). If the apertures are optically underfilled, it may suffice to actuate only the microlenses (FIG. 18C). On the other hand, if the apertures are overfilled with the diffraction-limited focus spots, then it may suffice to actuate only the apertures (FIG. 18D).

A mechanism for making small lateral adjustments in the source spot positions transverse to be spot beam axes (FIG. 18E) could be used, for example, to correct nanometer-scale overlay errors resulting from factors such as thermal gradients that cannot be corrected by a simple translation of the printing surface. This type of mechanism can be termed "spot alignment control."

Figure 18F:
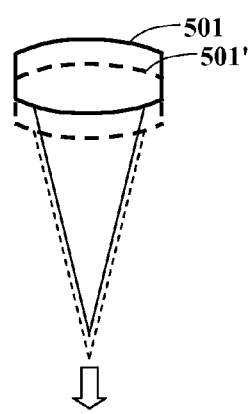

The spots could also (or alternatively) be actuated to move them axially, parallel to the spot beam axes (FIG. 18F). This type of actuation, which can be termed "spot focus control," could be used to enable conformal printing on non-flat printing surfaces.

In some embodiments, it may not be necessary to move the source spots individually, but it may be advantageous to move the entire spot-generation assembly as a unit. (The solid-immersion method discussed below could use this facility for scanning, or for alignment and fine-focus control.) Spot micro-positioning controls can be classified as "individual" or "collective" controls (e.g., individual or collective alignment control, individual or collective focus control) depending on whether they move the source spots individually or collectively.

Source Scanning

The entire spot-generation optical assembly (microlenses, spot-delimiting apertures, and aberration corrector elements) could be moved collectively to effect raster scanning of the spot images on the printing surface (or similarly, the inspection surface in a microscopy embodiment). The printing (or inspection) surface would not move during the scan process; it would only move to effect field stepping between scans. The continuous raster-scan pattern illustrated in FIG. 2 would not be used; instead the preferred scan pattern would be a simple bidirectional raster scan within each unit cell of the spot pattern, as illustrated in FIG. 19. The scan range of each spot is limited to a small area defined by a single unit cell in order to simplify the design requirements for the scan mechanism and projection optics.

FIG. 19 illustrates a number of spot images, such as spot 1901, on the printing (or inspection) surface 105 at a particular instant in time during the scan process. Each spot traces a multi-line, serpentine path such as path 1902 during the scan process. The scan-reversal portion of the path, indicated by dashed curves in FIG. 19, represents "dead time" during which the system is not printing (or acquiring image data). To optimize printing throughput and optical efficiency, it would be advantageous to shunt the radiation source between two print units, which are synchronized so that one is printing while the other is doing scan reversal. (The continuous line scan illustrated in FIG. 2 avoids the overhead of scan reversal, but is not compatible with source scanning.)

Although the projection lens's image distortion can be corrected by distributing the source spots on a non-uniform grid, the distortion could nevertheless result in raster line stitching errors between adjacent spots (e.g., spots 1901 and 1903) because the correction can only be exactly achieved for a particular scan position. The projection lens design could be constrained to substantially eliminate stitching errors. Alternatively, it may be advantageous to implement source scanning in conjunction with spot alignment control, which would effect dynamic distortion compensation during the scan process. The source-spot positioning layout would be defined to eliminate distortion at the center scan position, and the scan range would be defined to eliminate stitching errors at the center of the image field. Thus, the dynamic compensation mechanism would only need to make very small positioning adjustments.

Beam Scanning

Spot scanning can alternatively be effected by incorporating a beam scanning mechanism in the projection lens, as illustrated in FIG. 20. The mechanism is a type of "Risley wedge system," which is described by P. R. Yoder in chapter 7.3.26.2 of Ref 4. FIG. 20 is a schematic cross-section view of a spot-array imaging system comprising a projection lens 303, which images source-spot array 302 onto a conjugate image-spot array 104 on the printing or inspection surface 105. A beam scanner 2001, which is incorporated in the projection lens, comprises an X-scan subunit 2002 and a Y-scan subunit 2003. Each subunit comprises two counter-rotating optical disks in the beam path, such as X-scanning disks 2004 and 2005 in subunit 2002.

The X and Y scanners operate conjunctively to effect the bidirectional raster scan illustrated in FIG. 19, with the X-scanner effecting line scanning in the X direction, and the Y scanner effecting beam stepping in the Y direction between line scans. (Alternatively, a single Risley wedge system 2002 could be used to effect X scanning, while Y scanning is effected by mechanically translating the printing or inspection surface 105.)

FIG. 21 is a plan view of disks 2004 and 2005 in the X scanner 2002, which are both traversed by the projected beam. The beam aperture is indicated as 2101. Each disk is an optical wedge with a wedge angle perhaps on the order of 1 milliradian, which imparts a slight displacement in the position of each image spot on surface 105. (Alternatively, each disk could comprise a phase-Fresnel diffraction grating, with a Fresnel facet angle on the order of 1 milliradian and a grating period of order 1000 times the wavelength.) A single rotating disk would cause the focused spots to move in a circular path, and two counter-rotating disks in series (elements 2004 and 2005) would cause each spot to scan a straight line on surface 105. Two similar paired disks in the Y-scan unit are incrementally rotated during the X-scan reversal (dashed curves in FIG. 19) to effect Y displacement between successive X line scans.

FIG. 22 shows a plot of a particular spot's X coordinate on the surface 105 as a function of time t. X has a sinusoidal dependence on t. The dashed portions of the curve represent the scan reversal phase, during which time no printing or image acquisition occurs. (The source radiation could be shunted to another imaging unit during this phase.) During the active portion of the scan (solid portions of the curve) the spot scan speed is not uniform (assuming that the disk rotational speed is constant), so the image modulation (or image acquisition, in the context of microscopy) would need to be synchronized to the scanner in a manner that achieves uniform, distortion-free imaging. If a pulsed laser source is used, the pulse frequency (i.e., reciprocal pulse time interval) would need to dynamically vary in proportion to the scan speed $|dX/dt|$. If a continuous laser is used, then pulse-width modulation can be used to maintain exposure uniformity over the scan cycle. (Alternatively, the disk rotational speed could be dynamically controlled to maintain a uniform spot scan speed during the active portion of the scan. The disk surface shapes and projection optics design can also be optimized for uniform scan speed.)

As with source scanning, the beam-scan method may require that the projection optics design be constrained to achieve accurate line stitching between adjacent spots. However, this constraint could be removed if spot alignment control is implemented, allowing the source spot positions to be dynamically controlled to maintain null distortion over the entire scan range.

Solid Immersion

With the source-scan and X-Y beam-scan methods, the printing surface does not move relative to the projection lens during the scan process, and moves only to effect field stepping. This makes it possible to employ a solid-immersion imaging method in which the projection lens is optically coupled to the printing surface without any intervening nonsolid medium, except perhaps a very thin interface layer.

Figure 23:
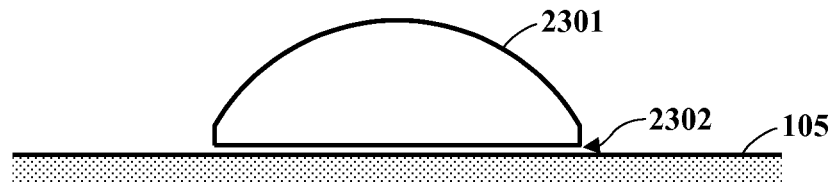
FIGS. 23, 24, 25, and 26 illustrate alternative embodiments of solid immersion lithography.

Solid immersion lithography is described in several prior-art publications such as B. W. Smith et al., Ref. 5, and D. Nam et al., Ref. 6. One way to implement solid immersion, illustrated in FIG. 23, would be to bring the last lens element 2301 of the projection lens (a plano-convex element) into very close proximity with the printing surface 105 (or inspection surface, in a microscopy application). In this mode of operation element 2301 can be termed a "solid-immersion lens." The element need not physically contact the surface, but it should be in sufficiently close proximity to enable efficient evanescent coupling of the focused radiation across the spacing gap 2302. (Optical rays that would normally be totally internally reflected at the bottom lens surface can efficiently traverse the gap if it is sufficiently thin.) The evanescent coupling efficiency could be enhanced by filling the gap with a high-index immersion fluid.

Figure 24:
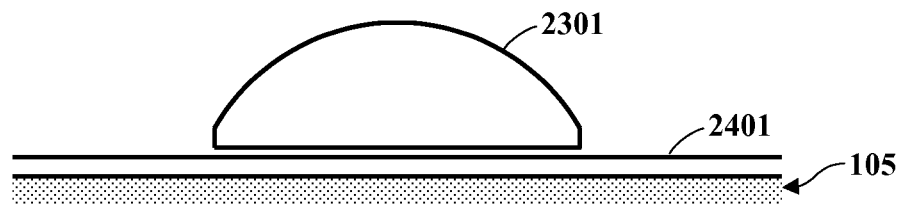

In an alternative, preferred approach illustrated in FIG. 24, a thin glass superstrate 2401 (several millimeters thick) is optically contacted to the printing surface 105, and the last lens element 2301 is brought into contact, or near-contact, with the superstrate. A vacuum seal could be used to maintain optical contact between the printing surface and superstrate throughout the printing process. The superstrate provides a barrier to cross-contamination between the printing surface and the projection system. It would be fabricated to stringent optical flatness and thickness tolerances to ensure efficient and uniform optical coupling between the lens and the superstrate, and also to accurately control focus height.

In some applications, the superstrate's bottom surface could itself be the printing surface. Rather than contacting the superstrate to a photoresist-coated printing surface, the photoresist could be coated directly on the superstrate's bottom surface, which could be subsequently etched to form a useful device such as a microlens array or a nanoimprint mold.

Figure 25:
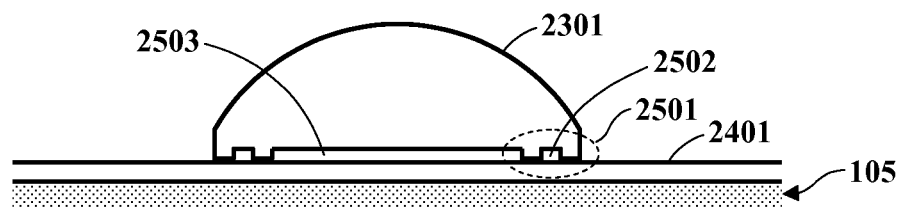

A possible embodiment of the FIG. 24 system is illustrated in greater detail in FIG. 25. The planar side of lens element 2301 (shown in cross-section) has an outer, annular flange 2501, which contacts the superstrate 2401. A vacuum seal may be formed by evacuating a circular channel 2502 in the flange. The inner portion of the lens surface is slightly recessed relative to the flange to create an interfacial air space 2503 of accurately controlled thickness (e.g., of order 10 nanometers or less). The air space is vented to ambient air pressure; or it may be pressure-regulated to keep the printing surface flat. The flatness could be measured by means of a confocal imaging system (e.g., of the type illustrated schematically in FIG. 13), which would also accurately measure focus and overlay across the image field. The spot-generation optics could be positionally actuated to eliminate focus and overlay errors before starting the exposure scan.

The system would be used in a step-and-scan mode in which separate image fields are sequentially scanned, with the printing surface and superstrate repositioned as a unit between scans. The air space 2503 in the FIG. 25 system functions to allow rapid field stepping. (If the full-aperture lens surface is directly contacted to the superstrate, it might take significant amount of time to first optically contact the surfaces, and then to release the contact.) An immersion fluid could possibly be used to improve optical coupling between the lens and the superstrate, but air coupling would be preferred.

Figure 26:
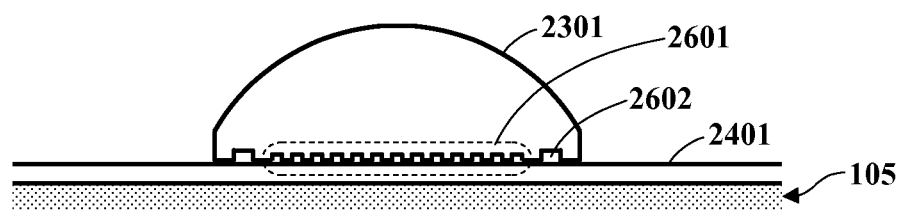

In an alternative approach, the full-aperture lens surface would be directly contacted to the superstrate, and some form of surface coating, or a microstructure formed on the lens or on the superstrate, would be used to facilitate rapid optical contacting and releasing of the surfaces. For example, FIG. 26 illustrates an embodiment in which the lens element 2301 has a biperiodic microstructure 2601 comprising, e.g., a matrix pattern of cylindrical posts formed on its flat surface. The microstructure creates a thin (e.g., less than 10 nanometers thick) interfacial air space between the posts. The microstructure's period is too small to significantly affect optical performance, but it would allow for rapid vacuum sealing and releasing the contact surfaces. During the exposure scan a peripheral channel 2602 would be evacuated to ensure efficient optical coupling and conformity of the printing surface to a flat focal plane; and after scanning positive air pressure may be applied through the channel to release the contact surfaces. (The interfacial air space is vented to the channel.)

Advantages of this approach are that it would automatically maintain very accurate focus control and would ensure efficient and uniform optical coupling between the lens and superstrate.

A step-and-scan system with solid immersion might spend only about half of its time scanning, with the remaining time allocated to field stepping. Furthermore, taking into account the scan reversal overhead, only about one quarter of the time would actually be spent exposing the printing surface. It would be advantageous to shunt the radiation source between four separate exposure systems to make full use of the available source power.

Lens materials that have been considered for the last lens element in 193-nm immersion lithography would also be good candidates for solid-immersion lithography. Two materials of particular interest are lutetium aluminum garnet ($Al_5Lu_3O_{12}$, abbr. "LuAG") and sapphire ($Al_2O_3$). The optical characteristics of these materials are detailed by J. H. Burnett et al., Ref. 7.

LuAG has a very high refractive index (2.144) at 193 nm. However, the material absorbance has not yet been improved to the requisite level for 193-nm immersion lithography. The development status of LuAG is reviewed by P. A. Zimmerman et al., Ref 8. Although LuAG does not yet meet requirements for 193-nm lithography, it could be used at a 266-nm wavelength, where its absorption is much lower. (See FIG. 2 in Zimmerman et al., Ref 8)

Sapphire has a high index of 1.932 at 193 nm, and is much closer to meeting 193-nm absorption requirements. (See Table 2 in Burnett et al., Ref. 7) Also, sapphire would be a good material for 266 nm (where its refractive index is 1.83), and its physical characteristics would be favorable for use as a superstrate material (element 2401 in FIGS. 24-26).

One complication of sapphire is that its high birefringence requires that the polarization state of the radiation incident on the last lens element be carefully controlled. The requisite polarization characteristics cannot be exactly achieved with conventional mask-projection systems, but can be achieved with spot-array imaging, as will be discussed below.

Burnett et al., cited below, also discuss a "spatial-dispersion-induced index anisotropy" characteristic of sapphire, which can have a small, but significant, effect on imaging performance. However, the aberration correction method of the present invention would automatically compensate for this effect if the aberration corrector design is adjusted to compensate for measured optical aberrations of the projection lens.

Polarization Control

In a lithography system that prints onto a horizontal surface, the projection lens's last lens element (e.g., element 2301 in FIGS. 23-26) is typically axisymmetric with a vertical optical axis. If the element is composed of a uniaxial crystal material such as sapphire or crystalline quartz, the crystal axis should be vertical (parallel to the optical axis), and the polarization state of the radiation should be controlled so that it is linearly polarized in a horizontal direction after transmitting into the crystal. This condition will avoid birefringence-induced beam splitting in the prism, and horizontal polarization is also generally preferred in order to minimize the diffraction-limited point spread of the focused spots.

The polarization constraint implies that meridional rays incident on the lens element's top surface should be linearly polarized perpendicular to the incidence plane (TE polarization). The incidence plane is vertical for meridional rays, so this condition ensures horizontal polarization. For skew rays, the optimal incident polarization state has a complex dependence on the ray geometry and the surface transmittance characteristics (e.g., the optimal state may be influenced by the presence of an antireflection coating on the lens surface).

Surface microstructures may be used to control and optimize the radiation's polarization characteristics. For example, wire-grid polarizers can be used to polarize UV radiation. Such structures are described by V. Pelletier et al., Ref. 9.

Figure 27:
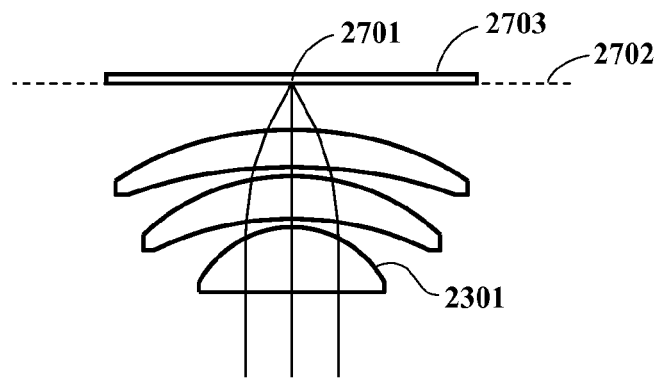
FIG. 27 illustrates an aperture polarization-control element in cross section, in the context of the projection optics.

The polarization constraint could be achieved, at least for meridional rays, by forming a pattern of radial wire grid elements on a surface that is conjugate to infinity in the image space. This surface coincides with the projection aperture plane in a telecentric projection lens. For example, FIG. 27 schematically illustrates several of the projection lens elements, including the last element 2301, which direct a ray bundle from point 2701 on projection aperture plane 2702 into vertically collimated rays within lens element 2301. Meridional rays can be horizontally polarized by means of an aperture polarization-control element 2703 comprising a wire-grid polarizer in or proximate the aperture plane. The element is shown in cross-section in FIG. 27 and in plan view in FIG. 28. The polarizer is a sub-wavelength pattern of radial, wire-grid elements, such as element 2801, comprising a UV-absorbing material such as aluminum or silicon. The polarizer absorbs radially-polarized light and transmits azimuthally-polarized light, as indicated by the azimuthally-directed arrows in FIG. 28. (The central portion 2802 of the polarization-control element may be masked.)

Figure 29:
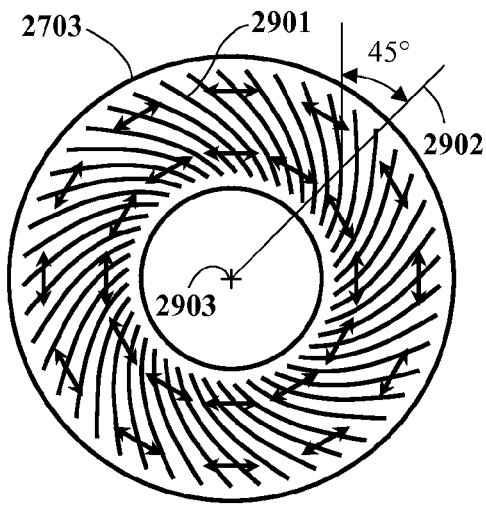
FIG. 29 illustrates an alternative type of aperture polarization-control element, a space-variant quarter-wave plate formed as a dielectric, sub-wavelength grating.

Surface microstructures can also be configured to operate as polarization-dependent phase retarders, e.g., as a quarter-wave plate. A space-variant quarter-wave plate, formed as a dielectric, sub-wavelength grating, can operate to convert circularly-polarized incident radiation into azimuthal linear polarization, as illustrated in FIG. 29. In this case the aperture polarization-control element 2703 comprises a lamellar, non-absorbing grating structure having curved grating lines such as line 2901, which form an angle of 45° with any radial vector 2902 through the optical axis 2903. An advantage of this type of system is that if the radiation source is polarized there is no loss of optical energy as there would be with a wire-grid polarizer.

Structures such as that illustrated in FIG. 29 are described by Z. Bomzon et al., Ref. 10. (FIG. 29 substantially replicates FIG. 1(*a*) in Bomzon.) The grating structures described by Bomzon are configured to operate in the infrared, but the same principle would apply to UV radiation. (Note: FIGS. 1(*b*) and 1(*c*) in Bomzon appear to misleadingly indicate that any two optical rays that are symmetrically opposed across the optical axis have amplitudes of opposite sign, but the exponential factor in Eq. (4) actually constrains them to have the same sign. For example, Eq. (4) has the same value at $\theta=0$ and $\theta=\pi$, implying preservation of phase coherence at the target focal point.)

The polarization-control mechanisms described above cannot exactly control the polarization to constrain all rays to be horizontally polarized within the last lens element 2301 because the local phase-modifying structure at any point on element 2703 can only be specified to achieve the requisite polarization for a particular ray traversing the point. The horizontal-polarization constraint would typically be achieved for meridional rays, but not for skew rays. However, a spot-array imaging system can be configured to achieve the polarization constraint for all rays, for the same reason that it can eliminate optical aberrations: In the non-overlap portion of the spot beams, each spatial point is traversed by only one geometric ray. Thus, a polarization-modifying surface structure located at any such point need only be designed to meet the polarization specification for a single ray.

It may be advantageous to use an aperture polarization-control element, such as the quarter-wave plate illustrated in FIG. 29, in conjunction with a polarization controller comprising individual controller elements for all of the source spots. (A wire-grid polarizer such as that of FIG. 28 should not be used because it would mask any polarization effects of any upstream polarization-control element.) This would simplify the design and manufacture of the polarization controller because it would only need to make small changes in the polarization state. However, it may also be feasible to construct the polarization controller to operate without the assistance of an aperture polarization-control element.

The positioning constraints on the polarization controller are the same as the aberration corrector, except that it must be located in the object space (region 404 in FIG. 4), not in the image space (region 405). It should be located at a position where the individual spot beams do not overlap, and within that constraint it should preferably be as far as possible from the source spots. There should be no intersection of geometric rays on the controller. The polarization controller may be formed integrally with the aberration corrector, e.g., as a sub-wavelength lamellar grating profile superimposed on a smooth surface profile that performs aberration correction. Or it could be formed on a separate surface in series with the aberration corrector.

The positioning options for the polarization controller are the same as the aberration corrector 403, as illustrated in FIGS. 5-9. It can be positioned after the spot-delimiting apertures (FIGS. 5, 6), between the microlenses and the apertures (FIG. 7), or before the microlenses (FIG. 8); or it could be formed integrally on the microlens surfaces (FIG. 9). The polarization controller would preferably be positioned before the apertures (FIGS. 7-9) so that any diffractive scatter from the surface microstructures is blocked. (Although such microstructures are commonly characterized as "sub-wavelength" the profile period actually need not be of sub-wavelength dimensions because any non-zero diffraction orders would be substantially blocked by the apertures.)

Figure 30:
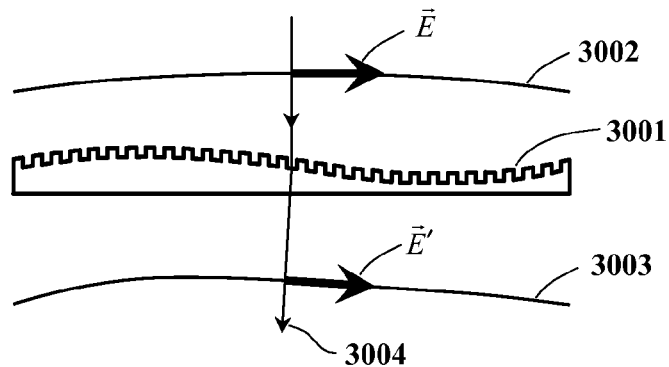
FIG. 30 schematically illustrates the operation of a spot polarization-control element.

The portion of the polarization controller traversed by any particular source-spot beam defines a spot polarization-control element, which is configured to ensure that all geometric rays traversing the element from the associated source spot are horizontally polarized at the image plane. FIG. 30 schematically illustrates the operation of a polarization-control element 3001 in cross-section. The element operates on a particular incident phase function, which is diagrammatically represented by incident geometric wave 3002 (a constant-phase surface). The element transforms the incident phase function into a transmitted phase function, represented by transmitted geometric wave 3003. The incident radiation is preferably polarized (e.g., circularly polarized), and is characterized by an incident complex electric field vector $\vec{E}$, which is a function of position across wave 3002 and is tangent to the wave. (If the incident radiation is not polarized, then the control element would need to incorporate a polarizing mechanism such as a wire-grid polarizer.) The transmitted radiation is similarly characterized by a complex electric field vector $\vec{E}'$, which is a function of position on wave 3003 and is tangent to the wave.

Geometric optical rays such as ray 3004 are paths perpendicular to the waves. The polarization-control element 3001 comprises a polarization-modifying microstructure whose form in the vicinity of any ray crossing is configured to convert a particular incident field vector $\vec{E}$ into a corresponding, specified transmitted field vector $\vec{E}'$. The microstructure may be formed on a curved substrate, as illustrated in the figure, to control the shape of wave 3003 and effect geometric aberration correction. The substrate shape may also have a phase-Fresnel form to effect narrow-band achromatization. In addition, a graded-thickness, optically absorbing layer may be incorporated in the optical path the control the beam intensity.

The incident and transmitted field vectors $\vec{E}$ and $\vec{E}'$ are defined by a procedure similar to that used to define the incident and transmitted phase functions for aberration correction. A polarization ray tracing procedure is used to trace rays from the radiation source through any optical elements preceding the polarization-control element. This determines $\vec{E}$. A reverse polarization ray tracing procedure is applied to trace rays from the target image point (where the rays are horizontally polarized) back through the projection lens and any intervening optics. This determines $\vec{E}'$. The polarization ray tracing takes into the account the effects of any surface coatings or polarization-modifying optical elements, and the specification of $\vec{E}$ and $\vec{E}'$ may be refined based on polarimetry measurements taken on the as-built optical system.

The phase-modifying microstructure could comprise a lamellar grating form similar to quarter-wave-plate gratings. The grating lines may be curved (as in the FIG. 29 illustration), and their dimensional characteristics may vary non-uniformly across the polarization-control element. A dielectric (non-absorbing) lamellar grating can impose a controlled phase shift between two linear polarization modes in the zero diffraction order without significantly affecting their relative intensities (assuming that there is not much energy loss into reflection or other diffraction orders).

If a partially absorbing material is used for the grating lines (or fills the grating spaces), then the grating can be configured to control both the relative phase and intensity between two linear polarization modes. These two degrees of freedom can be used to determine the polarization state of the transmitted beam. However, an absorbing material would not necessarily be required. A lossless dielectric grating can also generally be configured to achieve any output polarization state because the choice of the grating's rotational orientation provides an extra degree of freedom that obviates the need for an absorbing material.

The output beam's field vector $\vec{E}'$ has three complex-valued coordinate components, but there are only two independent components because $\vec{E}'$ is constrained to be tangent to the geometric wave 3003 in FIG. 30. The two independent complex components comprise four real values, which can be parmeterized in terms of the field's overall intensity ($|\vec{E}'|^2$), its overall phase (e.g., the average phase of two orthogonal polarization components), and two parameters related to the beam's polarization state (e.g., the phase difference and intensity ratio of two orthogonal polarization components). A dielectric grating can be configured to determine the beam's polarization state according to a defined specification, while the overall phase is controlled by a separate geometric aberration corrector element and the intensity is controlled by a separate intensity controller. (Alternatively, the grating design may have sufficient degrees of freedom to at least partially affect the overall phase or intensity, e.g., by incorporating a partially absorbing material in the grating.)

It is implicitly assumed in the above description that the incident and transmitted phase functions and wave shapes are polarization-independent, which would not be the case, for example, if there is some birefringence-induced polarization dispersion in the upstream optics. Nevertheless, the polarization controller, geometric aberration corrector, and intensity controller could have sufficient degrees of freedom to produce the specified $\vec{E}'$ output vector amplitude even in the presence of some polarization dispersion.

Multi-Function Optical Correction and Control Mechanisms

Figure 31A:
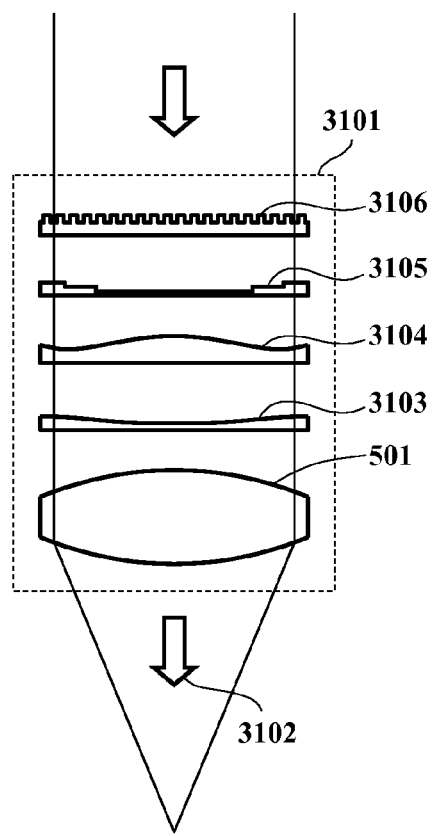
FIGS. 31A and 31B illustrate alternative embodiments of a spot-generation unit.
Figure 31B:
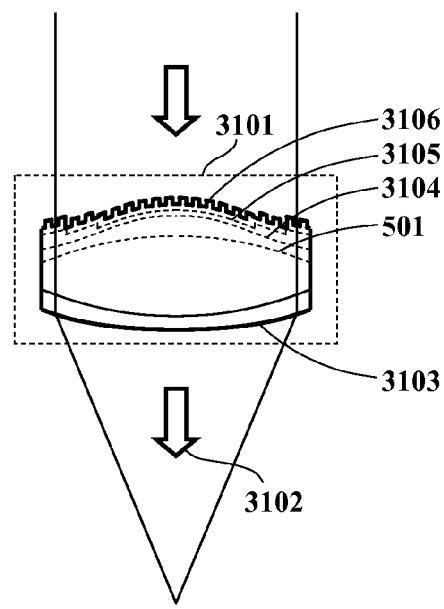

The optical correction and control mechanisms discussed above fall into four categories: (1) beam intensity control, (2) geometric aberration correction, (3) chromatic aberration correction and (4) polarization control. These mechanisms, in conjunction with the microlenses, constitute the spot-generation optics. Each source spot is formed by a portion of the spot-generation optics that can be termed a "spot-generation unit," which is traversed by an individual spot beam. The spot-generation units, or some elements in the units, may be mechanically actuated, either individually for each source spot or collectively for all spots, to effect spot alignment control and/or spot focus control, or to effect source scanning The spot-generation units can incorporate any or all of the four mechanisms, which can be formed on separate optical surfaces or can be combined in various combinations on multiple-function optical surfaces. FIGS. 31A and 31B schematically illustrate these mechanisms in two exemplary embodiments. FIG. 31A illustrates a spot-generation unit 3101, which transmits spot beam 3102 (indicated by block arrows), and which comprises the following elements: (1) a microlens 501, (2) a graded-thickness absorbing layer 3103, which controls the optical intensity distribution across the spot beam (e.g., to compensate for non-uniform transmittance of the microlenses or projection lens), (3) a graded-thickness, non-absorbing layer 3104, which performs geometric aberration correction, (4) a phase-Fresnel plate 3105, which performs chromatic aberration correction (i.e., narrow-band achromatization), and (5) a fine-pitch lamellar transmission grating 3106, which provides polarization control.

These mechanisms are illustrated as physically separate elements in FIG. 31A. FIG. 31B illustrates an alternative embodiment in which the absorbing layer 3103 is deposited on the bottom of microlens 501, and the geometric aberration corrector element 3104, chromatic aberration corrector element 3105, and polarization-control element 3106 are all formed integrally with the microlens's top surface. There are many other ways that the elements could be sequenced and combined.

All of the elements illustrated in FIGS. 31A and 31B can influence the overall optical phase of the transmitted beam, and the geometric aberration corrector 3104 would need to be designed to take those phase effects into account. Element 3104 is preferably non-absorbing, but it may exhibit some absorption, which must be taken into account in designing the intensity controller 3103. (For example, films 1507 and 1508 in FIG. 15 both exhibit EUV absorption.) In this case the functional distinction between elements 3103 and 3104 is unclear because they both influence phase and intensity, and their designs must be simultaneously optimized to achieve the specified phase and intensity. Thus, elements 3103 and 3104 may, in some cases, collectively constitute both the aberration corrector and intensity controller. Furthermore, the grating structure on element 3106 might also be configured to influence the beam's overall phase and amplitude, so the aberration corrector and intensity controller could potentially also comprise element 3106.

In the FIG. 31B embodiment, elements 501, 3104, 3105 and 3106 are not physically distinct, and are essentially separate summation terms in the microlens surface height function (as indicated by the dashed lines). In this case the top microlens surfaces would constitute the geometric aberration corrector, the chromatic aberration corrector, and the polarization controller.

Reflective Microlenses

As noted previously (under "EUV Embodiment") the term "lens" is used generically to denote refractive and/or reflective imaging systems. The term "microlens" can similarly denote a refractive and/or reflective micro-optic focusing device. In some embodiments of the invention the microlenses could be reflective elements (micromirrors), possibly in combination with proximate, optically transmitting structures (e.g., dielectric gratings) that perform the above-described functions.

Some elements of the projection lens could be used to direct illumination onto a reflective microlens array. For example, FIG. 32 illustrates a portion of the FIG. 3 or FIG. 4 apparatus in an alternative embodiment, in which an illumination beam 3201 is merged into the projection lens 303 by means of a diagonal mirror 3202 proximate the projection aperture plane, and is directed onto an array 301 of reflective microlenses comprising concave micromirror elements such as element 3203. Each micromirror converges the reflected radiation onto a source spot, such as spot 3204 corresponding to element 3203. The source spots may be aberrated to nullify projection lens aberrations. (Convex micromirrors may alternatively be used to diverge the reflected radiation from virtual source spots behind the micromirrors.)

All of the previously-described micro-optic functions (beam intensity control, geometric and chromatic aberration correction, polarization control) can be implemented by means of surface microstructures formed either on the reflective micromirror surfaces, or on transmitting optical microstructures formed on or proximate the micromirrors. An advantage of reflective micro-optics is that these functions could generally be performed with much shallower, low-profile structures than would be required with all-transmitting micro-optics.

Micromirrors have the disadvantage that the focused spots cannot be spatially filtered by means of apertures such as element 503 in FIGS. 5-9 because such apertures would interfere with the illumination optical path. However, this would not be problematic in confocal microscopy applications because the radiation collected from the image-plane focal spots on the inspection surface would be spatially filtered by an array of conjugate apertures in the collection optics. For example, FIG. 33 schematically illustrates a confocal microscope in which a beam splitter 3301 directs illumination 3201 onto spot-generation optics comprising a micromirror array 301, then transmits radiation from the source spots through projection optics to an inspection surface proximate focal plane 402, and then diverts radiation collected from the inspection surface onto an array 1309 of detector elements, each of which senses radiation from a corresponding image spot. An array 3302 of apertures conjugate to the image spots performs a spatial filtering function, obviating the need for an aperture array at the source spots.

Additional Detail on Achromatization

Phase-Fresnel lenses are described by K. Miyamoto, Ref 11. An application of such lenses for maskless lithography is described in U.S. Pat. No. 6,960,773, and applications for chromatic dispersion compensation are described in U.S. Pat. Nos. 5,161,057 and 5,589,982. A procedure for designing dispersion-compensating phase-Fresnel lenses is outlined below.

FIGS. 34A-B show cross-sectional views of a conventional, refracting lens surface 3401 (FIG. 34A) and a phase-Fresnel surface 3402 (FIG. 34B) comprising curved Fresnel facets f1, f2, . . . with facet boundaries b1, b2, . . . . In either case, the surface separates an index-n optical medium 3403 on the object side from an index-n' medium 3404 on the image side. For any particular wavelength, a specific object point gives rise to an electromagnetic field having a position-dependent phase $\Phi$ on the surface's object side, and the conjugate image point similarly has an associated phase function $\Phi'$ on the image side. (The phase functions increase in the field's direction of propagation and are each typically specified within an undetermined additive constant.) Geometric waves are constant-phase surfaces, and geometric rays are directed along the phase gradient.

The simple refracting surface geometry (FIG. 34A) is defined by a phase-matching criterion, Eq. 35.1 in FIG. 35. (All equations referred to in this section are in FIG. 35.) The "C" term in Eq. 35.1 is a constant, which is determined by specifying the location of a particular point on the surface. For a phase-Fresnel surface (FIG. 34B) that is blazed for maximum efficiency at a particular wavelength in the m-th diffraction order, an equation similar to Eq. 35.1 applies on the facet surfaces, except that the constant term jumps discontinuously by m2π between facets. This condition is stated in Eq. 35.2, where j is a sequential facet numbering index, e.g., 1, 2, . . . corresponding to f1, f2, . . . in FIGS. 34B, and C is a constant. (The plus sign in front of j in Eq. 35.2 could alternatively be minus, depending on the adopted sign conventions for indexing facets and diffraction orders.)

For an arbitrary wavelength, Eq. 35.2 does not generally hold, but it does hold on the facet boundaries for the m-th diffraction order's phase function $\Phi'$, as indicated in Eq. 35.3. (In this context, C is implicitly a position-independent function of wavelength.) The grating preserves phase coherence between corresponding points (e.g., boundary points) on different facets, although diffraction efficiency will generally be degraded due to dephasing between points on the same facet unless Eq. 35.2 holds. According to Eq. 35.3 the phase distribution $\Phi'$ in any particular diffraction order does not depend on the detailed surface geometry; it only depends on the geometry of the facet boundaries. The facet surface shape only determines the energy partitioning between diffraction orders.

A phase-Fresnel surface cannot be blazed for multiple wavelengths in a particular diffraction order, but Eq. 35.3 can be imposed for arbitrary specified phase functions $\Phi$ and $\Phi'$ at two distinct wavelengths, as described by Eqs. 35.4. $\Phi_1$ and $\Phi_1'$ are phase functions associated with a particular wavelength $\lambda_1$; $\Phi_2$ and $\Phi_1'$ are phase functions associated with a second wavelength $\lambda_2$; and $C_1$ and $C_2$ are distinct constants. The two equalities in Eqs. 35.4 define two surfaces whose intersection is a three-dimensional curve defining boundary j. (Boundaries b1, b2, . . . in FIG. 34B correspond to j=1, 2, . . . .) The difference between the two equalities defines the grating "substrate" (3405 in FIG. 34B), an imaginary smooth surface that includes the boundaries, Eq. 35.5.

The above design procedure achieves two-wavelength achromatization in diffraction order m at wavelengths $\lambda_1$ and $\lambda_2$. Narrow-band achromatization can be achieved by taking $\lambda_1$ and $\lambda_2$ to be infinitesimally close to the blaze wavelength, in which case Eq. 35.5 translates to a differential relation having of the form of Eq. 35.6. The conjunction of Eqs. 35.3 and 35.6 defines facet boundary j. The C term in Eq. 35.3 is "constant" in the sense of being position-independent, but it is wavelength-dependent. The dC/dλ term in Eq. 35.6 is defined (at the blaze wavelength) by specifying the location of any particular point on the substrate, and the C term in Eq. 35.3 is defined by specifying any particular facet boundary point on the substrate.

The preceding design principles can be adapted to reflective phase-Fresnel surfaces (e.g., formed on the micromirrors in the FIG. 32 system). In this case $\Phi'$ represents the reflected beam's phase distribution.

The design principles can be illustrated by applying them to a simple, periodic grating on a flat substrate, which operates to transform a plane-wave incident beam into a plane-wave transmitted beam. (More generally, this description applies approximately to any localized region of a grating over which the substrate curvature and grating aperiodicity are insignificant.) The incident beam has a phase function $\Phi[\lambda,x,y]$, as a function of wavelength $\lambda$ and Cartesian position coordinates x and y, as described by Eq. 35.7. (x and y are coordinates in a plane defined by the incident and transmitted rays at the blaze wavelength.) n[λ] is the refractive index in the incident medium (as a function of λ) and θ[λ] is the incidence beam's propagation angle (which may also be a function of wavelength).

(Note: This disclosure follows the Mathematica convention of using square braces "[ . . . ]" to delimit function arguments and using round braces "( . . . )" only for grouping.). The transmitted beam (in a particular diffraction order) similarly has a phase function $\Phi'[\lambda,x,y]$ described by Eq. 35.8, where n'[λ] is the refractive index in the transmitted medium and θ'[λ] is the transmitted beam's propagation angle.

The λ dependence of θ[λ] results from chromatic dispersion of optical elements preceding the grating in the optical path, and the λ dependence of θ'[λ] can be specified to offset and neutralize dispersion in any elements following the grating, as well as those preceding it. For narrow-band operation, the propagation angles θ and θ' are specified at a particular blaze wavelength for which the grating is optimized, and the system's dispersion characteristics are defined by the angle derivatives with respect to wavelength, dθ/dλ and dθ'/dλ. The grating substrate orientation is defined by Eq. 35.6 to achieve the dispersion specification. Substitution of Eqs. 35.7-8 into Eq.s 35.6 yields Eq. 35.9, where the " . . . " sub-expression represents terms that are independent of x and y. These terms collectively constitute a constant, whose value is determined by specifying a point on the substrate; and Eq. 35.9 then defines the substrate geometry.

Figure 36:
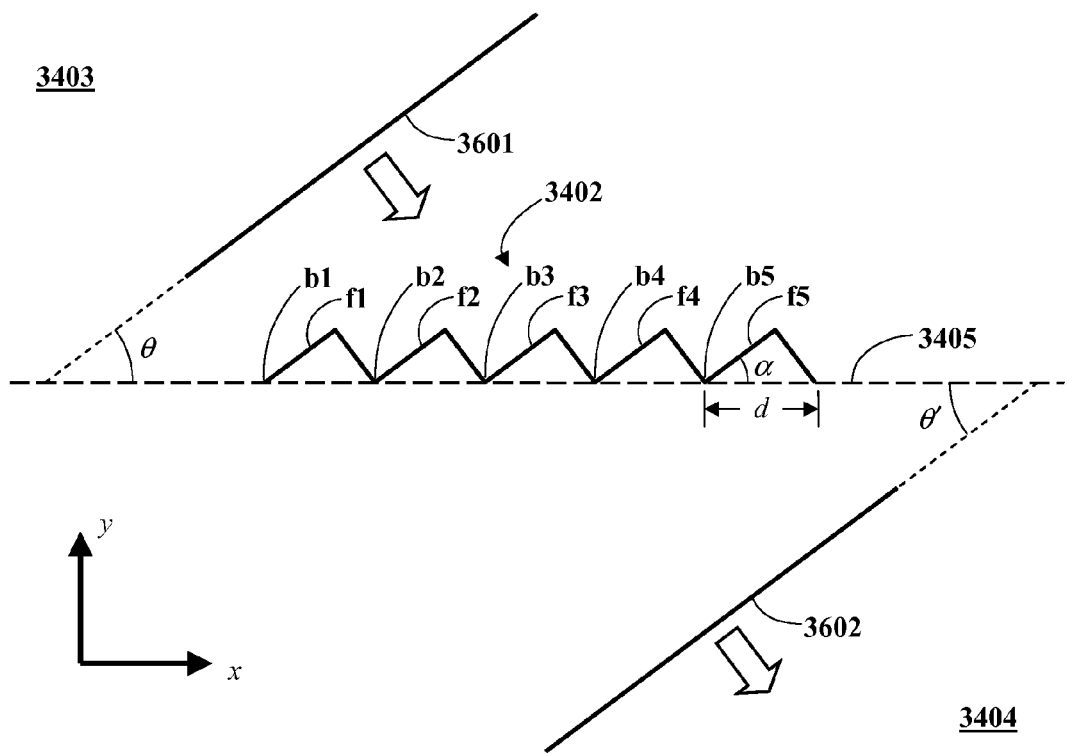
FIG. 36 illustrates the cross-sectional geometry of a blazed, phase-Fresnel grating.

After the substrate orientation is determined, the grating geometry can be described relative to (x, y) coordinates with the x direction parallel to the substrate and the y direction pointing toward the object side of the grating, as illustrated in FIG. 36. The propagation angles θ and θ' are redefined so that Eqs. 35.7-8 still hold relative to the substrate-aligned coordinates. The figure illustrates a representative wavefront 3601 (at angle θ to the substrate 3405) in the incident medium 3403, and a representative wavefront 3602 (at angle θ' to the substrate) in the transmitted medium 3404.

The grating has a faceted, sawtooth form, and the j-th facet boundary coordinates are denoted as $(x_j,y_j)$ (e.g., boundary b1 is at $(x,y)=(x_1,y_1)$, b2 is at $(x,y)=(x_2,y_2)$, etc.; FIG. 36). The coordinates are defined by Eq. 35.10, where d is the grating period (FIG. 36). Eqs. 35.7, 35.8, and 35.10 are substituted into Eq. 35.3 to obtain Eq. 35.11, where the " . . . " sub-expression represents terms that are independent of j. The entire expression vanishes for all j; hence the grating equation, Eq. 35.12, is obtained. (For the zero order, m=0, this reduces to Snell's Law applied on the substrate.) With θ and θ' specified at the blaze wavelength, Eq. 35.12 determines d, and the equation thereafter determines θ' as a function of θ for any wavelength. (d may be formally defined as a negative quantity, depending on the adopted sign convention for diffraction order indexing.)

The grating facet angle is α (FIG. 36), and the relationship between x and y on facet j is defined by Eq. 35.13. This relationship is substituted into Eq. 35.2, along with Eqs. 35.7 and 35.8, to obtain Eq. 35.14, where $\lambda_B$ is the order-m blaze wavelength and the " . . . " sub-expression represents terms that are independent of x. The entire expression vanishes for all x within the range of facet j; hence the blaze condition, Eq. 35.15, is obtained. This is equivalent to Snell's Law applied on the facet surfaces. Eq. 35.15 can be solved for the blaze angle α, Eq. 35.16.

Eqs. 35.7-35.16 can be adapted for a reflection grating by formally defining n'=−n and adopting a θ' sign convention with θ'=θ in a Littrow configuration. An advantage of reflection gratings is that they can perform a specified dispersion-compensation function with a comparatively shallow grating profile, and with much less light loss and scatter into extraneous diffraction orders.

Figure 37A:
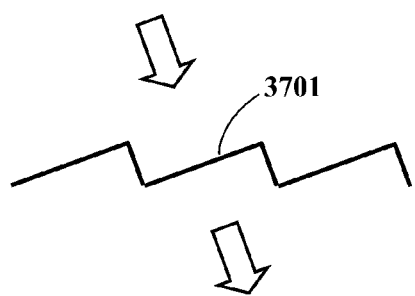
FIGS. 37A and 37B illustrate two types of blazed, phase-Fresnel gratings, a transmission grating and a reflection grating.
Figure 37B:
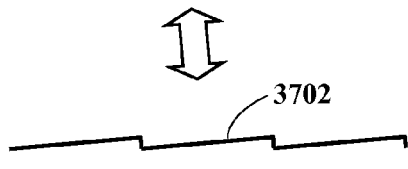

For example, FIGS. 37A and 37B illustrate two diffraction gratings, a transmission grating 3701 (FIG. 37A) and a reflection grating 3702 (FIG. 37B), which are both designed for a blaze wavelength of 0.266 μm incident from a direction normal to the facet surfaces. For the transmission grating, the beam transmits from an index-1.5 medium into air (n=1.5, n'=1). For the reflection grating, the external medium is air (n=1, n'=−1) and the grating medium is aluminum (with complex refractive index 0.217+3.18 i). The transmission grating transmits the blaze wavelength without deviation, whereas the reflection grating retroreflects the blaze wavelength (Littrow configuration). The propagation angles θ and θ', and facet angle α, are defined by Eq. 35.17 for this configuration. (The gratings both operate in the—1st order; m=−1 in Eq. 35.17.) Both gratings have a 1.5-μm period, so they exhibit very similar dispersion characteristics.

Figures 38A, 38B, 39:
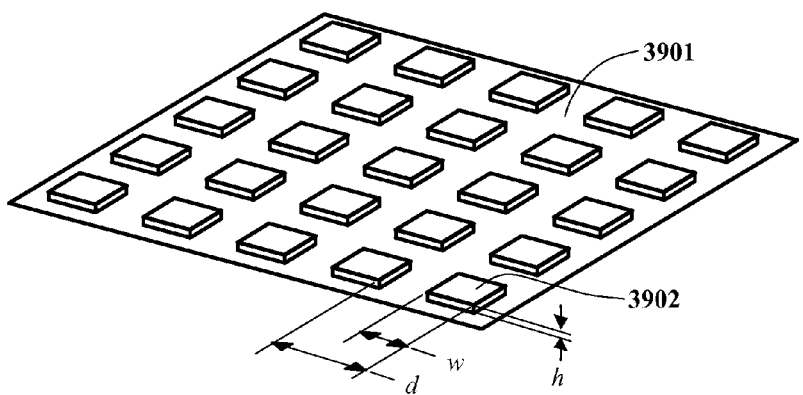
FIGS. 38A and 38B tabulate multi-order diffraction efficiency data for the two gratings of FIGS. 37A and 37B.
FIG. 39 illustrates a surface texturing pattern for a solid-immersion lens.

Design and performance data for the two gratings are summarized in FIG. 38A (for the transmission grating) and FIG. 38B (for the reflection grating). (The data in FIGS. 38A and 38B were calculated using a boundary-integral method similar to that described by R. Petit et al., Ref 14.) Calculated diffraction efficiencies are tabulated for all non-evanescent diffraction orders, and for both TE and TM polarization. The row labeled "scattered" represents the portion of incident energy in transmitted orders (FIG. 38A), or reflected orders (FIG. 38B), other than the blaze order. The reflection grating's blaze angle α is about one-quarter that of the transmission grating, and its light scatter into extraneous diffraction orders is significantly less. The transmission grating's scatter could be greatly reduced by using a high-refractive-index grating material, and the reflection grating's scatter could be reduced by immersing it in a high-index dielectric medium (e.g., by aluminizing a fused-silica grating surface).

The grating structures illustrated in FIGS. 37A and 37B were modeled as simple sawtooth profiles with flat surfaces and sharp, right-angle facet and trough corners. In practice, the design can include some corner rounding to improve manufacturability, and the surfaces can have some curvature to optimize diffraction efficiency and minimize light scatter into extraneous orders. The scatter would not necessarily be problematic for grating elements within the spot-generation optics because the blaze order can be filtered by apertures such as element 503 in FIGS. 5-9. Such apertures could not be used with reflection gratings, but in the context of confocal microscopy the image spots could be spatially filtered by the aperture array 3302 in FIG. 33.

Additional Detail on Solid Immersion

Following are some simulation results illustrating the optical coupling efficiency between the solid immersion lens 2301 and superstrate 2401 in FIGS. 24-26. A wavelength of 0.266 μm is assumed, and the lens and superstrate are both sapphire (refractive index 1.83). The interfacial space between the lens and superstrate is air.

For the FIG. 26 configuration, the bottom lens surface is modeled as a textured surface of the form illustrated in FIG. 39. The surface 3901 comprises shallow, square-section pillars such as pillar element 3902, which directly contact the superstrate during the printing process. The surface pattern is biperiodic, with period d=0.050 μm, and the pillars have width dimensions w=0.025 μm. The pillar height, h, is varied between zero and 0.020 μm in the simulations.

Figure 40:
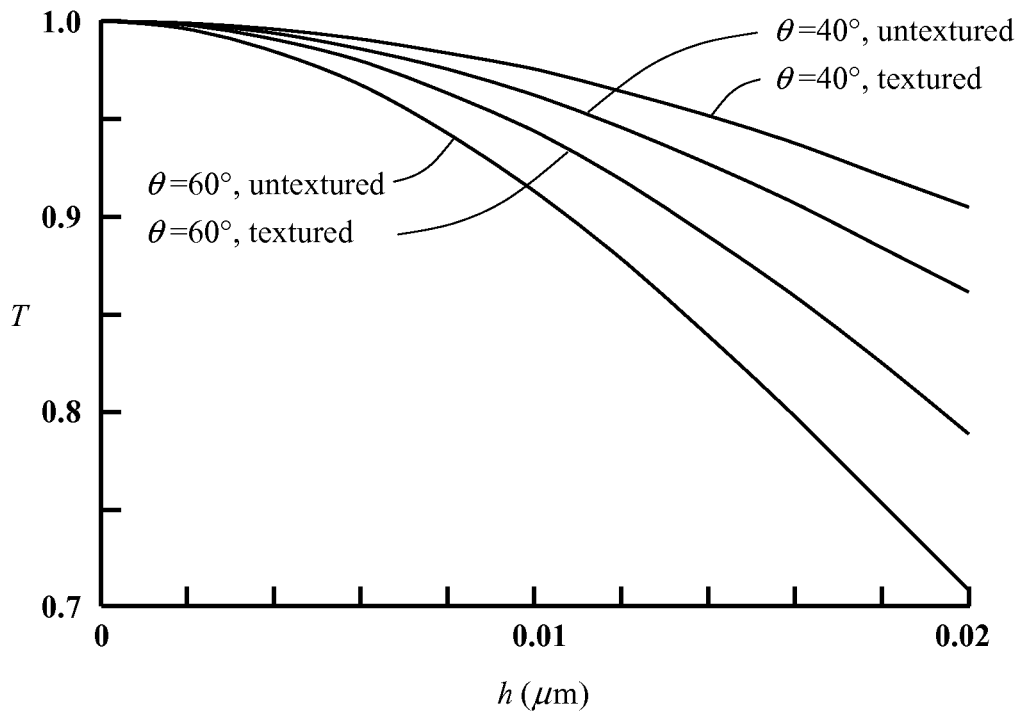
FIG. 40 plots a solid immersion lens's interfacial transmission efficiency versus gap height for two internal incidence angles, with and without surface texturing.

FIG. 40 shows a plot of the optical transmission efficiency T between the lens and superstrate, as a function of gap height h, for a collimated beam polarized parallel to the superstrate. Several plots are illustrated for the following conditions: for an internal incident angle θ of 40° or 60°, and for either an untextured surface (FIGS. 24 and 25) or a textured surface (FIGS. 26 and 39). For example, at θ=60° and h=0.010 μm the transmission efficiency is 91.4% without texturing and 94.4% with texturing. (The data in FIG. 40 were calculated using a commercial grating simulation program, GD-Calc, Ref 13.)

Additional Detail on Polarization Control

Phase-modifying surface microstructures such as those illustrated in FIG. 29, FIG. 30 (element 3001) and FIGS. 31A and 31B (element 3106) are described by I. Richter et al., Ref. 12. Richter describes a variety of grating forms (e.g., lamellar, sinusoidal, trapezoidal) and design methodologies that would be applicable to the polarization-control devices described herein.

Figure 41:
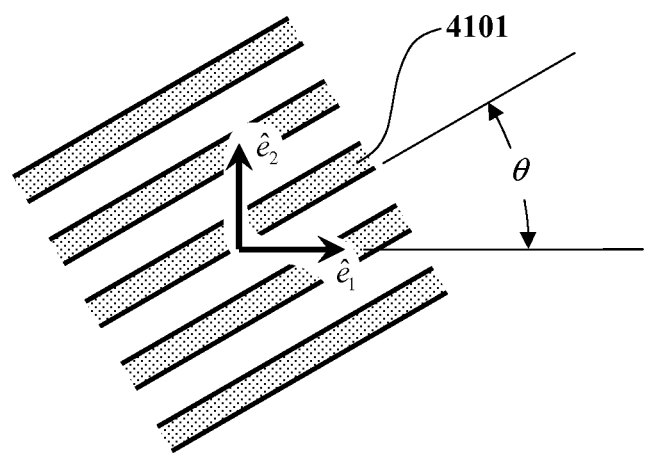
FIG. 41 is a plan view of a form-birefringent grating in relation to coordinate basis vectors.

As described previously, a polarization-control device is designed to convert an incident electric field vector $\vec{E}$ into a transmitted field vector $\vec{E}'$ with a specified polarization state (FIG. 30). (For the present discussion we are considering transmission devices. Similar design principles apply to reflection micro-optics such as the micromirror 3203 in FIG. 32, which could be configured to control polarization by means of a form-birefringent dielectric grating formed on the mirror surface.) The operation of a form-birefringent polarization-control element can be illustrated by considering, for simplicity, a grating that operates on a normally-incident collimated beam. $\vec{E}$ and $\vec{E}'$ are specified in relation to orthonormal basis vectors $\hat{e}_1$ and $\hat{e}_2$, which are parallel to the grating substrate. As illustrated in FIG. 41, the grating lines (such as line 4101) are rotated by an angle θ from to $\hat{e}_1$ toward $\hat{e}_2$. $\vec{E}$ and $\vec{E}'$ are defined by Eqs. 42.1 and 42.2 in FIG. 42, wherein $E_1$, $E_2$, $E_1'$ and $E_2'$ are complex-valued scalar amplitudes. (All equations referred to in this section are in FIG. 42.)

The incident and transmitted fields are related by a Jones matrix transformation having the form of Eq. 42.3, where $t_1$ is the grating's complex amplitude transmittance for radiation that is linearly polarized parallel to the grating lines (TE polarization), and $t_2$ is its complex amplitude transmittance for radiation polarized perpendicular to the lines (TM polarization). For an ideal form-birefringent phase plate $t_1$ and $t_2$ would have the same magnitude and would differ only in phase, but in practice they may differ in magnitude even if the device has no optical absorption, because the phase plate may exhibit polarization-dependent reflection losses.

The incident and transmitted fields' polarization states are described by the complex amplitude ratios $P=E_1/E_2$ and $P'=E_1'/E_2'$ (Eqs. 42.4-5). It follows from Eq. 42.3 that P, P', θ, and the ratio $\rho=t_1/t_2$ (Eq. 42.6) satisfy a relationship described by Eq. 42.7. The real and imaginary parts of this relationship define two design conditions that should be satisfied by selection of ρ and θ. Since ρ is complex-valued, the grating design has an extra degree of freedom that can be used to satisfy another design condition (e.g., controlling the transmitted beam intensity).

Eq. 42.7 (or a generalization of the equation that applies to non-normal incidence) can be used to design either the polarization-control elements in the spot-generation optics (element 3106 in FIG. 31) or an aperture phase plate in the projection lens (FIG. 29). For example, FIG. 43 illustrates a radial section 4301 of the polarization-control element 2703 in FIG. 29, along a line 4302 through axial point 2903 and parallel to basis vector $\hat{e}_1$. The grating geometry over any localized region 4303 at radial displacement r from axis 2903 resembles that of FIG. 41, and is defined by the condition that circularly polarized incident illumination should be converted to transmitted radiation that is linearly polarized parallel to $\hat{e}_2$. Eqs. 42.1-2 and 42.7 reduce to Eq. 42.8 for this case.

If the grating is configured to balance the transmittance intensity between TE and TM polarizations (i.e., $|\rho|=1$), then Eq. 42.8 implies that $\theta=45°$, as illustrated in FIG. 29. However, there is no need to impose this condition because any intensity mismatch between TE and TM can be accommodated by setting $\tan[\theta]=|\rho|$ according to Eq. 42.8. In any case, Eq. 42.8 implies that the grating would induce a 45° phase shift between the TE and TM polarization modes.

Figures 44, 45:
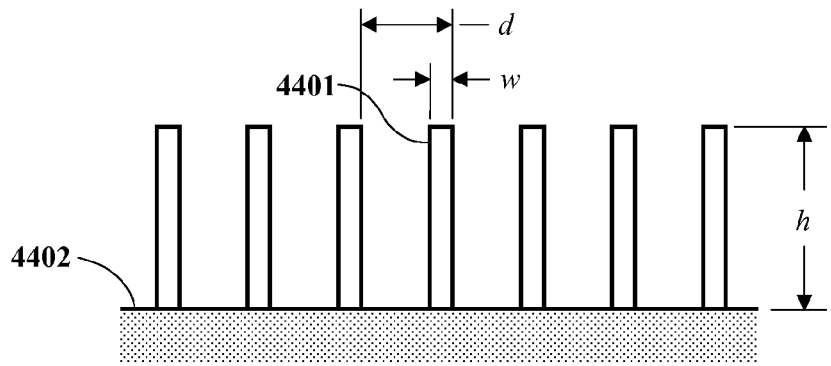
FIG. 44 illustrates the cross-sectional geometry of a particular type of form-birefringent grating.
FIG. 45 tabulates design and optical performance data for a form-birefringent grating that is configured to achieve uniform optical transmittance efficiency.

FIG. 44 illustrates a cross-sectional profile of one type of form-birefringent grating structure that would be useful for polarization control. The device consists of lamellar nitride ($Si_3N_4$) lines, such as line 4401, on a fused silica ($SiO_2$) substrate 4402. (The grating can operate with the incident beam coming from either the air side or the substrate side.) The grating's geometry parameters are its period (d), line width (w), and height (h). FIG. 45 tabulates design and optical performance data for a grating having the form of FIG. 44, based on an operating wavelength of 0.266 μm, and assuming refractive indices of 1.5 for $SiO_2$ and 2.2 for $Si_3N_4$. For each d value h and w are selected to satisfy two conditions: The grating-induced phase shift between TE and TM ("arg[ρ]" column) should be 90°, and the polarization-averaged intensity transmittance ("T" column) should be independent of d. The tabulated $|\rho|$ values determine θ according to Eq. 42.8 ($|\sigma|=\tan[\theta]$). The "phase" values represent the grating-induced phase shift, averaged over TE and TM polarizations. This represents a wavefront distortion, which must be compensated for, e.g., by tailoring the grating substrate's thickness profile to compensate for the nonuniform phase shift.

The grating design outlined in FIG. 45 would be useful for the aperture phase plate of FIGS. 29 and 43, which comprises a range of grating periods increasing from the center to the outer edge of the aperture. The period d is constrained by Eq. 42.9, which relates d over region 4303 in FIG. 43 to the local grating rotation angle $f$, the radial position r, and the total number N of curved grating lines on the device. (d and θ are functions of r.) θ is eliminated between Eqs. 42.8 and 42.9 to obtain Eq. 42.10. The period d at the inner edge of the grating would be set to the minimum manufacturable dimension (e.g., 0.05 μm); $|\rho|$ would be defined at the inner edge based on the design data in FIG. 45; and N would be determined from Eq. 42.10. (A slight adjustment in d would be made to make N integer-valued.) Once N is determined, the period d is determined at any r position from Eq. 42.10, in combination with the FIG. 45 data, which defines $|\rho|$ as function of d.

The data in FIG. 45 were calculated using a commercial grating simulation program, GD-Calc, Ref 13 (including evanescent diffraction orders up to order 50 in the simulations). For each d and w combination, h was determined to make the phase shift arg[ρ] equal to 90°, and subject to this constraint the w values were chosen to make the transmission efficiency T independent of d. The latter objective was achieved by representing the w/d ratio as a quartic interpolated polynomial function of d between five fitting points, and optimizing the fitting points to minimize the variance of T over a dense (2 nm) sampling of d values ranging from 0.05 μm to 0.15 μm. Optimizing w/d independently for each d value would lead to numerical instabilities because the w/d-versus-d relation traverses a saddle point on T versus d and w/d. (The saddle point is at d=0.136 μm, w/d=0.189.) The quartic fit avoids this instability.

The constancy of T versus d ensures that the grating preserves the intensity profile of the incident beam in the transmitted beam. In an alternative design approach, T could be constrained to vary with d in a manner that imposes an optimal radial transmittance profile on the grating. Or T could be unconstrained and the grating could be configured to achieve other design objectives, such as optimizing manufacturability. For example, FIG. 46 illustrates design data for the form-birefringent grating of FIG. 44 in which w is chosen to minimize h. In this case, intensity control could be provided by an intensity controller in the spot-generation optics, which could be more easily controlled to stringent tolerances. (This will be discussed in the next section.)

Polarization-control elements could be incorporated in the spot-generation optics, in lieu of an aperture phase plate, using elements having a form similar to that of FIGS. 44-46. But it would be preferable to use both in combination. The aperture phase plate would optimize the polarization state at the center of the image field, and the spot-generation micro-optics would make comparatively small corrections to optimize the polarization state for off-center image points (and perhaps also to compensate for imperfections in the aperture phase plate). In this case, the micro-optic polarization control elements could simply comprise etched gratings in fused silica (not in nitride). A form-birefringent quarter-wave plate formed in fused silica would be extremely deep (e.g., 0.7 μm for an operating wavelength of 0.266 μm), but if the spot-generation optics only induce comparatively small polarization phase shifts they would comprise much shallower gratings.

Additional Detail on Intensity Control

The transmitted $\vec{E}'$ field, as defined by Eq. 42.2, comprises two complex-valued scalar components $E_1'$ and $\vec{E}_2'$, each of which comprises two real values. The scalar components can be represented in terms of their magnitude and phase, as indicated in Eqs. 42.11-12 (FIG. 42). $\vec{E}'$ can be further defined in terms of four scalar quantities: $\frac{1}{2}(\phi_1'+\phi_2')$, $(\phi_1'-\phi_2')$, $|E_1'/E_2'|$, and $|E_1'|^2+|E_2'|^2$, as indicated in Eqs. 42.13-14. The first of these quantities, the average phase of $E_1'$ and $E_2'$, is determined by the aberration corrector (element 3104 in FIGS. 31A and 31B). The second and third quantities are defined by P' (Eqs. 42.5 and 42.15), which can be determined with a polarization controller (element 3106). The last term, which represents the total power in the transmitted field, can be determined by an intensity controller (element 3103).

The intensity controller can be a graded-thickness absorbing layer, as described previously. Alternatively, it could be a diffractive attenuator comprising a non-absorbing diffraction grating, which attenuates the zero-order intensity by shunting energy into first and higher diffraction orders. (The spot-delimiting apertures 503 in FIGS. 5-9 would block the diffracted energy; or in the absence of such apertures the projection lens's limiting aperture could block the diffracted orders.) If a polarization-neutral attenuator is needed, then a biperiodic grating such as a square array of circular posts could be used, as illustrated in FIG. 47. However, there would be no need to require polarization neutrality if the optics include polarization control. Polarization and intensity control could be provided by a single optical surface such as that illustrated in FIG. 48. The surface comprises a superposition of two crossed grating patterns, a sub-wavelength grating that exhibits form birefringence for polarization control, and a coarse grating pattern that diffractively attenuates the zero order. The gratings' structural parameters (e.g., line orientation, line width, depth) could vary nonuniformly across the grating aperture to provide full control over the E-field's spatial distribution.

REFERENCES

The following additional patent and literature references are referred to in this disclosure and are incorporated by reference:

U.S. Pat. No. 5,161,057 November 1992 Johnson
U.S. Pat. No. 5,589,982 December 1996 Faklis et al.
U.S. Pat. No. 6,133,986 October 2000 Johnson
U.S. Pat. No. 6,331,710 December 2001 Wang
U.S. Pat. No. 6,498,685 December 2002 Johnson
U.S. Pat. No. 6,639,201 October 2003 Almogy
U.S. Pat. No. 6,897,941 May 2005 Almogy
U.S. Pat. No. 6,960,773 November 2005 Menon et al.
U.S. Pat. No. 7,116,405 October 2006 Johnson
Ref. 1: M. Fritze, B. Tyrrell, D. Astolfi, D. Yost, P. Davis, B. Wheeler, R. Mallen, J. Jarmolowicz, and S. Cann, "Gratings of regular arrays and trim exposures for ultralarge scale integrated circuit phase-shift lithography," J. Vac. Sci. Technol. B 19(6), 2366-2370 (2001).
Ref. 2: H-Y. Tsai, H. I. Smith, and R. Menon, "Fabrication of spiral-phase diffractive elements using scanning-electron beam-lithography," J. Vac. Sci. Technol. B 25, pp. 2068-2071 (2007)
Ref. 3: D. C. Brandt, I. V. Fomenkov, A. I. Ershov, W. N. Pardo, D. W. Myers, N. R. Böwering, A. N. Bykanov, G. O. Vaschenko, O. V. Khodykin, J. R. Hoffman, E. Vargas L., R. D. Simmons, J. A. Chavez, and C. P. Chrobak, "LPP EUV Source Development for HVM," in Proc. of SPIE Vol. 6517, Emerging Lithographic Technologies XI, M. J. Lercel, Ed., 65170Q (2007).
Ref. 4: P. R. Yoder, "Opto-Mechanical Systems Design, Third Edition," CRC Press (2006).
Ref. 5: B. W. Smith, Y. Fan, M. Slocum; L. Zavyalova, "25 nm Immersion Lithography at a 193 nm Wavelength," Proc. SPIE 5745, pp. 141-147 (2004).
Ref. 6: D. Nam, T. D. Milster, and T. Chen, "Potential of Solid Immersion Lithography using I-line and KrF light source," Proc. SPIE 5745, pp. 1049-1055 (2005).
Ref. 7: J. H. Burnett, E. C. Benck, S. G. Kaplan, G. Y. Sirat, and C. Mack, "Birefringence issues with uniaxial crystals as last lens elements for high-index immersion lithography," Proc. SPIE 7274, pp. 727421-1 . . . 11 (2008).
Ref. 8: P. A. Zimmerman, B. J. Rice, E. C. Piscani, and V. Liberman, "High Index 193 nm Immersion Lithography: The Beginning or the End of the Road," Proc. SPIE 7274, pp. 727420-1 . . . 11 (2009).
Ref. 9: V. Pelletier, K. Asakawa, M. Wu, D. H. Adamson, R. A. Register, P. M. Chaikin, "Aluminum nanowire polarizing grids: Fabrication and analysis," Appl. Phys. Lett. 88, pp. 211114-1 . . . 3 (2006).
Ref. 10: Z. Bomzon, G. Biener, V. Kleiner, and E. Hasman, "Radially and azimuthally polarized beams generated by space-variant dielectric subwavelength gratings," Optics Letters 27(5), pp. 285-287 (2002).
Ref. 11: K. Miyamoto, "The Phase Fresnel Lens," J. Opt. Soc. Am. 51(1), pp. 17-20 (1961).
Ref. 12: I. Richter, P. C. Sun, F. Xu, and Y. Fainman, "Design considerations of form birefringent microstructures," Applied Optics 34(14), pp. 2421-2429 (1995).
Ref. 13: GD-Calc® (Grating Diffraction Calculator), http://software.kjinnovation.com/GD-Calc.html.
Ref. 14: R. Petit, M. Cadilhac, D. Maystre, P. Vincent, M. Nevière, R. C. McPhedran, G. H. Derrick, and L. C. Botten, "Electromagnetic Theory of Gratings," R. Petit, ed. (Springer-Verlag, Berlin, 1980).

Conclusion

The above disclosure is directed primarily toward scanned-spot-array lithography, but the mechanisms and methods are also applicable to scanned-spot-array microscopy.

While the above is a complete description of specific embodiments of the invention, the above description should not be taken as limiting the scope of the invention as defined by the claims.

What is claimed is:

1. A spot-array imaging system comprising a projection lens and an aberration corrector, wherein:
    the system is configured to simultaneously convey each of a plurality of optical radiation beams to an image surface, and to focus each beam to a diffraction-limited focus spot at a corresponding image point on the image surface;
    the aberration corrector comprises a phase-modifying optical surface or plurality of phase-modifying optical surfaces, and is disposed in a position where the beams are substantially non-overlapping and not in focus; and
    each beam traverses a portion of the aberration corrector, which is configured to compensate for any point-imaging optical aberrations of the projection lens so that the aberration corrector and the projection lens in combination achieve substantially aberration-free point focusing of each beam at its corresponding image point.

2. The spot-array imaging system of claim 1, further comprising a microlens array, wherein:
    each beam comprises radiation traversing a corresponding microlens;
    each microlens converts radiation incident on the microlens into a substantially point-convergent or point-divergent beam; and
    the portion of the aberration corrector that is traversed by any particular beam is further configured to compensate for any point-imaging optical aberrations of the corresponding beam-forming microlens so that the microlens array, the aberration corrector, and the projection lens in combination achieve substantially aberration-free point focusing of each beam at its corresponding image point.

3. The spot-array imaging system of claim 2, wherein:
    the image surface is planar;
    the microlenses have focal points disposed on a non-planar object surface; and
    the object surface has a geometric form that compensates for any field curvature of the projection lens.

4. The spot-array imaging system of claim 3, wherein
    the image points on the image surface form a periodic grid;
    the microlens focal points are located at points of a non-periodic grid; and
    the non-periodicity of the non-periodic grid compensates for any image distortion by the projection lens.

5. The spot-array imaging system of claim 2, wherein the microlenses are refractive lenses.

6. The spot-array imaging system of claim 1, further comprising a microlens array, wherein:
the aberration corrector is the microlens array and each phase-modifying surface of the aberration corrector is a microlens surface in the microlens array;
each beam comprises radiation traversing a corresponding microlens;
each microlens converts radiation incident on the microlens into a substantially point-convergent or point-divergent beam; and
the microlens array and the projection lens in combination achieve substantially aberration-free point focusing of each beam at its corresponding image point.

7. The spot-array imaging system of claim 2, wherein the microlenses are diffractive zone-plate lenses.

8. The spot-array imaging system of claim 6, wherein the microlenses are zone-plate lenses having zones that are configured to compensate for any point-imaging optical aberrations of the projection lens.

9. The spot-array imaging system of claim 2, wherein the microlenses are phase-Fresnel lenses.

10. The spot-array imaging system of claim 6, wherein the microlenses are phase-Fresnel lenses that are configured to compensate for any point-imaging optical aberrations of the projection lens.

11. The spot-array imaging system of claim 2, wherein the microlenses are reflective micromirrors.

12. The spot-array imaging system of claim 6, wherein the microlenses are reflective micromirrors that are configured to compensate for any point-imaging optical aberrations of the projection lens.

13. A spot-array imaging system comprising a projection lens and a beam intensity controller, wherein:
the system is configured to simultaneously convey each of a plurality of optical radiation beams to an image surface, and to focus each beam to a diffraction-limited focus spot at a corresponding image point on the image surface;
the beam intensity controller comprises an optically attenuating layer or surface, or plurality of optically attenuating layers or surfaces, and is disposed in a position where the beams are substantially non-overlapping and not in focus; and
each beam traverses a portion of the beam intensity controller, and has an optical intensity distribution after the traversal;
the beam intensity controller is configured to individually control the optical intensity distribution across each beam and to equalize intensity levels between focus spots on the image surface.

14. The spot-array imaging system of claim 13, further comprising a microlens array, wherein:
each beam comprises radiation traversing a corresponding microlens, and has a transmittance intensity distribution after traversal;
each microlens converts radiation incident on the microlens into a substantially point-convergent or point-divergent beam; and
the portion of the beam intensity controller that is traversed by any particular beam is further configured to compensate for any non-uniformity in the transmittance intensity of the corresponding beam-forming microlens.

15. The spot-array imaging system of claim 14, wherein the beam intensity controller comprises an optically absorptive layer deposited on each microlens.

16. The spot-array imaging system of claim 14, wherein
the beam intensity controller comprises a diffraction grating formed on each microlens,
the projection lens conveys zero-order radiation from each grating to the image surface, and
the intensity controller attenuates the zero diffraction order by shunting energy into other diffraction orders.

17. A spot-array imaging system comprising a projection lens and an achromatizer, wherein:
the system is configured to simultaneously convey each of a plurality of optical radiation beams to an image surface, and to focus each beam to a diffraction-limited focus spot at a corresponding image point on the image surface;
the optical radiation comprises a band of radiation wavelengths;
the achromatizer comprises a phase-Fresnel optical surface or plurality of phase-Fresnel surfaces, and is disposed in a position where the beams are substantially non-overlapping and not in focus; and
each beam traverses a portion of the achromatizer, which is configured to compensate for any point-imaging chromatic aberration of the projection lens so that the achromatizer and the projection lens in combination achieve substantially achromatic point focusing of each beam at its corresponding image point.

18. The spot-array imaging system of claim 17, further comprising a microlens array, wherein:
each beam comprises radiation traversing a corresponding microlens;
each microlens converts radiation incident on the microlens into a substantially point-convergent or point-divergent beam; and
the portion of the achromatizer that is traversed by any particular beam is further configured to compensate for any chromatic aberrations of the corresponding beam-forming microlens so that the microlens array, the achromatizer, and the projection lens in combination achieve substantially achromatic point focusing of each beam at its corresponding image point.

19. The spot-array imaging system of claim 18, wherein the achromatizer comprises a phase-Fresnel surface formed on each microlens.

20. A spot-array imaging system comprising a projection lens and polarization controller, wherein:
the system is configured to simultaneously convey each of a plurality of optical radiation beams to an image surface, and to focus each beam to a diffraction-limited focus spot at a corresponding image point on the image surface;
the polarization controller comprises a form-birefringent grating microstructure surface or plurality of form-birefringent grating microstructure surfaces, and is disposed in a position where the beams are substantially non-overlapping and not in focus; and
each beam traverses a portion of the polarization controller, which is configured to control the beam's polarization state so that at the image surface the beam is polarized substantially parallel to the image surface.

21. The spot-array imaging system of claim 20, further comprising a microlens array, wherein:
each beam comprises radiation traversing a corresponding microlens;
each microlens converts radiation incident on the microlens into a substantially point-convergent or point-divergent beam; and the portion of the polarization controller that is traversed by any particular beam compensates for any polarization effects of the corresponding beam-forming microlens so that the beam is substantially horizontally polarized at the image surface.

22. The spot-array imaging system of claim 21, wherein the polarization controller comprises a form-birefringent grating microstructure formed on each microlens.

23. The spot-array imaging system of claim 1, claim 13, claim 17, or claim 20, which further comprises a scanning mechanism and one or more optical modulators, and is further configured to print a lithographic image on a photosensitive layer, wherein:
the image surface is planar;
the focus spots form a periodic array on the image surface;
the scanning mechanism is configured to effect a scan operation by establishing relative motion between the focus spots and the photosensitive layer when the photosensitive layer is positioned proximate the image surface, wherein, as a result of the relative motion, the focus spots traverse paths relative to the photosensitive layer comprising a set of raster lines on the photosensitive layer; and
the optical modulators modulate the beams in synchronization with the scan operation, whereby a synthesized, high-resolution raster image can be recorded on the photosensitive layer.

24. The spot-array imaging system of claim 23, wherein the beams are individually modulated by separate optical modulators.

25. The spot-array imaging system of claim 23, wherein the beams are not individually modulated, but are collectively modulated by a single optical modulator.

26. The spot-array imaging system of claim 23, wherein each focus spot is conjugate to a corresponding radiation source spot that is imaged by the system onto the focus spot, and the scanning mechanism effects scanning by establishing relative motion between the corresponding radiation source spots and the projection lens.

27. The spot-array imaging system of claim 23, wherein the scanning mechanism comprises a Risley wedge system of counter-rotating wedge disks disposed in the optical path within the projection lens.

28. The spot-array imaging system of claim 23, wherein:
the projection system comprises a last lens element that is proximate the image surface, and which does not move relative to the printing surface during the scan operation; and
during the scan operation, the last lens element either contacts the printing surface or is positioned sufficiently close to the printing surface to allow efficient evanescent coupling of radiation from within the last lens element to the printing surface.

29. The spot-array imaging system of claim 23, wherein:
the photosensitive layer is contacted to a transparent superstrate during the scan operation;
the projection lens comprises a last lens element that is proximate the superstrate during the scan operation, and which does not move relative to the superstrate and printing surface during the scan operation; and
during the scan operation, the last lens element either contacts the superstrate or is positioned sufficiently close to the superstrate to allow efficient evanescent coupling of radiation from within the last lens element into the superstrate.

30. The spot-array imaging system of claim 1, claim 13, claim 17, or claim 20, which further comprises a scanning mechanism and an array of optical detector elements, and is further configured to construct a microscopic image of an inspection surface, wherein:
the image surface is planar;
the focus spots form a periodic array on the image surface;
the scanning mechanism is configured to effect a scan operation by establishing relative motion between the focus spots and the inspection surface when the inspection surface is positioned proximate the image surface, wherein, as a result of the relative motion, the focus spots traverse paths relative to the photosensitive layer comprising a set of raster lines on the inspection surface; and
the system is further configured to collect radiation reflected from or transmitted through the inspection surface at the focus spots and direct the collected radiation from each focus spot onto a corresponding detector element, whereby a high-resolution raster image of the inspection surface can be synthesized from optical signals acquired from the detector elements in synchronization with the scan operation.

31. The spot-array imaging system of claim 30, wherein each focus spot is conjugate to a corresponding radiation source spot that is imaged by the system onto the focus spot, and the scanning mechanism effects scanning by establishing relative motion between the source spots and the projection lens.

32. The spot-array imaging system of claim 30, wherein the scanning mechanism comprises a Risley wedge system of counter-rotating wedge disks disposed within the projection lens.

33. The spot-array imaging system of claim 30, wherein:
the projection system comprises a last lens element that is proximate the image surface, and which does not move relative to the inspection surface during the scan operation; and
during the scan operation, the last lens element either contacts the inspection surface or is positioned sufficiently close to the inspection surface to allow efficient evanescent coupling of radiation between the last lens element and the inspection surface.

34. The spot-array imaging system of claim 30, wherein:
the inspection surface is contacted to a transparent superstrate during the scan operation;
the projection lens comprises a last lens element that is proximate the superstrate during the scan operation, and which does not move relative to the superstrate and inspection surface during the scan operation; and
during the scan operation, the last lens element either contacts the superstrate or is positioned sufficiently close to the superstrate to allow efficient evanescent coupling of radiation between the last lens element and the superstrate.

35. The spot-array imaging system of claim 6, wherein the microlenses are refractive lenses having optical surfaces that are configured to compensate for any point-imaging optical aberrations of the projection lens.

* * * * *